(12) United States Patent
Cohen

(10) Patent No.: US 12,263,299 B2
(45) Date of Patent: Apr. 1, 2025

(54) DEVICES AND METHODS FOR CESSATION OF NICOTINE ADDICTION

(71) Applicant: JUUL Labs, Inc., San Francisco, CA (US)

(72) Inventor: Gal A. Cohen, Mill Valley, CA (US)

(73) Assignee: JUUL Labs, Inc., Washington, DC (US)

( * ) Notice: Subject to any disclaimer, the term of this patent is extended or adjusted under 35 U.S.C. 154(b) by 813 days.

(21) Appl. No.: 16/453,110

(22) Filed: Jun. 26, 2019

(65) Prior Publication Data

US 2019/0387796 A1    Dec. 26, 2019

Related U.S. Application Data

(60) Provisional application No. 62/690,271, filed on Jun. 26, 2018.

(51) Int. Cl.
*A24F 40/30* (2020.01)
*A24F 40/42* (2020.01)
(Continued)

(52) U.S. Cl.
CPC ............. *A61M 15/06* (2013.01); *A24F 40/30* (2020.01); *A24F 40/42* (2020.01); *A24F 40/50* (2020.01);
(Continued)

(58) Field of Classification Search
CPC .......... A24F 40/65; A24F 40/30; A24F 40/42; A24F 40/40; A24F 40/20; A24F 40/50
See application file for complete search history.

(56) References Cited

U.S. PATENT DOCUMENTS 5,610,635 A    3/1997  Murray et al.
8,402,976 B2   3/2013  Fernando et al.
(Continued)

FOREIGN PATENT DOCUMENTS

CN    201067079 Y    6/2008
CN    104321779 A    1/2015
(Continued)

OTHER PUBLICATIONS

Behm, et al., (Jan. 1993) Clinical Evaluation of a Citric Acid Inhaler for Smoking Cessation, Drug and Alcohol Dependence, 31(2):131-138.
(Continued)

*Primary Examiner* — Alex B Efta
(74) *Attorney, Agent, or Firm* — Mintz Levin Cohn Ferris Glovsky and Popeo, P.C.

(57) ABSTRACT

Vaporizers and vaporizer systems, which can include a device in communication with a vaporizer, can include one or more features related to control of functions and/or features of the vaporizer. A method for operating a vaporizer device is provided. The method includes determining a delivery pattern for providing a first puff containing an amount of a first vaporizable material and a second puff containing an amount of a second vaporizable material. The first vaporizable material includes a first substance and the second vaporizable material does not include the first substance. The method further includes providing a plurality of puffs from a vaporizer. The plurality of puffs based on the delivery pattern and including the first puff and the second puff. The method further includes receiving user feedback associated with the delivery pattern in response to the providing. The method further includes modifying the delivery pattern based on the user feedback.

24 Claims, 11 Drawing Sheets

(51) Int. Cl.
*A24F 40/50* (2020.01)
*A24F 40/65* (2020.01)
*A61M 11/04* (2006.01)
*A61M 15/06* (2006.01)

(52) U.S. Cl.
CPC ........... *A24F 40/65* (2020.01); *A61M 11/042* (2014.02); *A61M 2205/50* (2013.01); *A61M 2205/8206* (2013.01)

(56) References Cited

U.S. PATENT DOCUMENTS

| | | |
|---|---|---|
| 8,550,069 B2 | 10/2013 | Alelov |
| 8,807,131 B1 | 8/2014 | Tunnell et al. |
| 9,439,455 B2 | 9/2016 | Alarcon et al. |
| 9,462,832 B2 | 10/2016 | Lord |
| 9,609,895 B2 | 4/2017 | Galloway et al. |
| 9,770,055 B2 | 9/2017 | Cameron et al. |
| 9,877,519 B2 | 1/2018 | Xiang |
| 10,058,124 B2 | 8/2018 | Monsees et al. |
| 10,131,532 B2 | 11/2018 | Murison et al. |
| 10,375,990 B2 | 8/2019 | Lord |
| 10,448,670 B2 | 10/2019 | Talon et al. |
| 10,945,463 B2 | 3/2021 | Dickens et al. |
| 2005/0066961 A1 | 3/2005 | Rand |
| 2009/0266358 A1 | 10/2009 | Rock et al. |
| 2010/0191385 A1 | 7/2010 | Goodnow et al. |
| 2010/0234987 A1 | 9/2010 | Benschop et al. |
| 2011/0036346 A1 | 2/2011 | Cohen et al. |
| 2011/0097060 A1 | 4/2011 | Buzzetti |
| 2011/0150294 A1 | 6/2011 | Eckhoff et al. |
| 2012/0291791 A1 | 11/2012 | Pradeep |
| 2012/0304990 A1 | 12/2012 | Todd |
| 2013/0220315 A1 | 8/2013 | Conley et al. |
| 2013/0284192 A1 | 10/2013 | Peleg et al. |
| 2013/0311001 A1 | 11/2013 | Hampiholi |
| 2013/0319439 A1 | 12/2013 | Gorelick et al. |
| 2013/0340775 A1 | 12/2013 | Juster et al. |
| 2014/0078164 A1 | 3/2014 | Chan et al. |
| 2014/0123989 A1 | 5/2014 | Lamothe |
| 2014/0144429 A1* | 5/2014 | Wensley ............... A61M 15/06 128/200.14 |
| 2014/0182608 A1 | 7/2014 | Egoyants et al. |
| 2014/0190496 A1 | 7/2014 | Wensley et al. |
| 2014/0246035 A1 | 9/2014 | Minskoff et al. |
| 2014/0278250 A1 | 9/2014 | Smith et al. |
| 2014/0283859 A1 | 9/2014 | Minskoff et al. |
| 2014/0334804 A1 | 11/2014 | Choi |
| 2014/0338685 A1 | 11/2014 | Amir |
| 2014/0345635 A1 | 11/2014 | Rabinowitz et al. |
| 2015/0020822 A1* | 1/2015 | Janardhan ............ A61M 15/06 131/328 |
| 2015/0020825 A1 | 1/2015 | Galloway et al. |
| 2015/0064672 A1* | 3/2015 | Bars .................. G01N 33/4972 434/236 |
| 2015/0101625 A1 | 4/2015 | Newton et al. |
| 2015/0114407 A1 | 4/2015 | Duncan et al. |
| 2015/0122252 A1 | 5/2015 | Frija |
| 2015/0136155 A1 | 5/2015 | Verleur et al. |
| 2015/0136158 A1 | 5/2015 | Stevens et al. |
| 2015/0164144 A1 | 6/2015 | Liu |
| 2015/0181945 A1 | 7/2015 | Tremblay |
| 2015/0208731 A1 | 7/2015 | Malamud et al. |
| 2015/0216237 A1 | 8/2015 | Wensley et al. |
| 2015/0257445 A1 | 9/2015 | Henry et al. |
| 2015/0258289 A1 | 9/2015 | Henry et al. |
| 2015/0272220 A1 | 10/2015 | Spinka et al. |
| 2015/0272223 A1 | 10/2015 | Weigensberg et al. |
| 2015/0288468 A1 | 10/2015 | Xiang |
| 2015/0305409 A1 | 10/2015 | Verleur et al. |
| 2015/0359263 A1 | 12/2015 | Bellinger |
| 2016/0004469 A1 | 1/2016 | Yun et al. |
| 2016/0021930 A1 | 1/2016 | Minskoff et al. |
| 2016/0057811 A1 | 2/2016 | Alarcon et al. |
| 2016/0063235 A1 | 3/2016 | Tussy |
| 2016/0089508 A1 | 3/2016 | Smith et al. |
| 2016/0106936 A1* | 4/2016 | Kimmel ............... A24F 40/485 392/404 |
| 2016/0143361 A1 | 5/2016 | Juster et al. |
| 2016/0157524 A1 | 6/2016 | Bowen et al. |
| 2016/0161459 A1 | 6/2016 | Rouse |
| 2016/0166786 A1 | 6/2016 | Kinzer |
| 2016/0198767 A1 | 7/2016 | Verleur |
| 2016/0219933 A1 | 8/2016 | Henry et al. |
| 2016/0219938 A1* | 8/2016 | Mamoun ................. G05B 15/02 |
| 2016/0221930 A1 | 8/2016 | Minskoff et al. |
| 2016/0278435 A1 | 9/2016 | Choukroun et al. |
| 2016/0331026 A1 | 11/2016 | Cameron |
| 2016/0331036 A1* | 11/2016 | Cameron ................. H04Q 9/00 |
| 2016/0331859 A1 | 11/2016 | Cameron |
| 2016/0360789 A1 | 12/2016 | Hawes et al. |
| 2016/0363570 A1 | 12/2016 | Blackley |
| 2016/0366946 A1 | 12/2016 | Murison et al. |
| 2017/0018000 A1 | 1/2017 | Cameron |
| 2017/0034324 A1 | 2/2017 | Zhang et al. |
| 2017/0042230 A1 | 2/2017 | Cameron |
| 2017/0042252 A1* | 2/2017 | Takeuchi ................ A24F 40/53 |
| 2017/0046357 A1 | 2/2017 | Cameron |
| 2017/0048691 A1 | 2/2017 | Liu |
| 2017/0135408 A1 | 5/2017 | Cameron |
| 2017/0136193 A1 | 5/2017 | Cameron |
| 2017/0156397 A1 | 6/2017 | Sur et al. |
| 2017/0157341 A1 | 6/2017 | Pandya et al. |
| 2017/0180067 A1 | 6/2017 | Poornachandran et al. |
| 2017/0181474 A1 | 6/2017 | Cameron |
| 2017/0196270 A1 | 7/2017 | Vick et al. |
| 2017/0208867 A1 | 7/2017 | Li et al. |
| 2017/0215480 A1 | 8/2017 | Qiu |
| 2017/0231273 A1 | 8/2017 | Xiang |
| 2017/0245550 A1 | 8/2017 | Freelander |
| 2017/0258136 A1 | 9/2017 | Hawes et al. |
| 2017/0262064 A1 | 9/2017 | Ofir et al. |
| 2017/0266397 A1 | 9/2017 | Mayle et al. |
| 2017/0273357 A1 | 9/2017 | Barbuck |
| 2017/0304563 A1 | 10/2017 | Adelson |
| 2017/0304567 A1 | 10/2017 | Adelson |
| 2017/0318861 A1 | 11/2017 | Thorens |
| 2017/0360097 A1 | 12/2017 | Xiang |
| 2017/0368273 A1 | 12/2017 | Rubin |
| 2018/0020720 A1 | 1/2018 | Matischek et al. |
| 2018/0043114 A1 | 2/2018 | Bowen et al. |
| 2018/0132526 A1 | 5/2018 | Davis et al. |
| 2018/0153219 A1 | 6/2018 | Verleur et al. |
| 2018/0153221 A1 | 6/2018 | Verleur et al. |
| 2018/0160733 A1 | 6/2018 | Leadley et al. |
| 2018/0184722 A1 | 7/2018 | Murison et al. |
| 2018/0325176 A1* | 11/2018 | Burseg ................. A24F 40/50 |
| 2019/0104762 A1 | 4/2019 | Cameron |
| 2019/0158938 A1 | 5/2019 | Bowen et al. |
| 2019/0272359 A1 | 9/2019 | Popplewell et al. |
| 2019/0307170 A1 | 10/2019 | Zarifian et al. |
| 2020/0058057 A1 | 2/2020 | Ouyang |
| 2021/0011446 A1 | 1/2021 | Anderson et al. |

FOREIGN PATENT DOCUMENTS

| | | |
|---|---|---|
| CN | 204275207 U | 4/2015 |
| CN | 104797152 A | 7/2015 |
| CN | 204466899 U | 7/2015 |
| CN | 104839892 B | 8/2015 |
| CN | 105050434 A | 11/2015 |
| CN | 105342009 B | 2/2016 |
| CN | 105722417 A | 6/2016 |
| CN | 106164958 A | 11/2016 |
| CN | 106455717 A | 2/2017 |
| CN | 106462862 A | 2/2017 |
| CN | 106573118 A | 4/2017 |
| CN | 106573123 A | 4/2017 |
| CN | 106594797 A | 4/2017 |
| CN | 106686995 A | 5/2017 |
| CN | 106998821 A | 8/2017 |
| CN | 107438372 A | 12/2017 |
| CN | 108038161 A | 5/2018 |
| CN | 111213920 A | 6/2020 |

(56) References Cited

FOREIGN PATENT DOCUMENTS

| | | |
|---|---|---|
| CN | 212464894 U | 2/2021 |
| EP | 2110034 A1 | 10/2009 |
| EP | 2399636 A1 | 12/2011 |
| EP | 3000245 B1 | 3/2016 |
| EP | 3463535 B1 | 8/2022 |
| GB | 2507103 A | 4/2014 |
| GB | 2527403 A | 12/2015 |
| GR | 20120100199 A | 11/2013 |
| JP | 2949114 B1 | 9/1999 |
| JP | 2006180378 A | 7/2006 |
| JP | 2007172605 A | 7/2007 |
| JP | 2008501406 A | 1/2008 |
| JP | 2008059382 A | 3/2008 |
| JP | 2013524835 A | 6/2013 |
| JP | 2016114402 A | 6/2016 |
| JP | 2017513513 A | 6/2017 |
| JP | 2019521739 A | 8/2019 |
| KR | 10-2009-0119127 A | 11/2009 |
| KR | 10-2010-0080114 A | 7/2010 |
| KR | 101523088 B1 | 5/2015 |
| KR | 20150064754 A | 6/2015 |
| KR | 102535301 | 10/2021 |
| RU | 2606942 C2 | 1/2017 |
| TW | 201330884 A | 8/2013 |
| TW | M548451 U | 9/2017 |
| TW | 1763672 B | 5/2022 |
| WO | WO-2011160788 A1 | 12/2011 |
| WO | WO-2014058678 A1 | 4/2014 |
| WO | WO-2014060267 A2 | 4/2014 |
| WO | WO-2014068504 A2 | 5/2014 |
| WO | WO-2015031836 A1 | 3/2015 |
| WO | WO-2015038981 A2 | 3/2015 |
| WO | WO-2015063126 A1 | 5/2015 |
| WO | WO-2015138560 A1 | 9/2015 |
| WO | WO-2015161485 A1 | 10/2015 |
| WO | WO-2015161486 A1 | 10/2015 |
| WO | WO-2015165747 A1 | 11/2015 |
| WO | WO-2015167000 A1 | 11/2015 |
| WO | WO-2016008096 A1 | 1/2016 |
| WO | WO-2016009202 A1 | 1/2016 |
| WO | WO-2016058992 A2 | 4/2016 |
| WO | WO-2016065413 A1 | 5/2016 |
| WO | WO-2016123307 A1 | 8/2016 |
| WO | WO-2016187110 A1 | 11/2016 |
| WO | WO-2017054627 A1 | 4/2017 |
| WO | WO-2017055801 A1 | 4/2017 |
| WO | WO-2017056103 A1 | 4/2017 |
| WO | WO-2017205692 A1 | 11/2017 |
| WO | WO-2020006311 A1 | 1/2020 |

OTHER PUBLICATIONS

Grotenhermen, et al., (Sep. 2005) "Developing Science-Based Per Se Limits for Driving under the Influence of Cannabis (DUIC)—Findings and Recommendations by an Expert Panel", Canorml, Available at: http://www.canorml.org/healthfacts/DUICreport. 2005, 49 pages.

Pham, et al., (Feb. 28, 2011) "A Clustering Approach for Collaborative Filtering Recommendation Using Social Network Analysis", Journal of Universal Computer Science, 17(4):583-604.

* cited by examiner

200

DEVICES AND METHODS FOR CESSATION OF NICOTINE ADDICTION

CROSS REFERENCE TO RELATED APPLICATIONS

This application claims priority to U.S. Application No. 62/690,271, filed on Jun. 26, 2018, and entitled "DEVICES AND METHODS FOR CESSATION OF NICOTINE ADDICTION", the disclosure of which is incorporated herein by reference.

TECHNICAL FIELD

The apparatuses, devices, systems, and methods described herein relate to aerosolizing or vaporizing devices, such as ENDS (electronic nicotine delivery systems), and to methods of using, controlling, making, such devices. The apparatuses, devices, systems, and methods may optionally be configured to provide or include providing information to a user indicating an amount of vapor consumed.

BACKGROUND

Aerosolizing devices, which can also be referred to as electronic vaporizer devices or e-vaporizer devices, can be used for delivery of vapor containing one or more active ingredients by inhalation of the vapor by a user of the vaporizing device. Electronic vaporizer devices are gaining increasing popularity both for prescriptive medical use, in delivering medicaments, and for consumption of tobacco and other plant-based smokable materials. Electronic vaporizer devices in particular may be portable, self-contained and convenient for use. Typically, such devices are controlled by one or more switches, buttons or the like (controls) on the vaporizer, although a number of devices that may wirelessly communicate with an external controller (e.g., smartphone) have recently become available.

SUMMARY

Aspects of the current subject matter relate to management of operation (e.g., one or more settings or operation parameters) of a vaporizer.

In some aspects, a computer-implemented method for operating a vaporizer device is provided. The method includes determining a delivery pattern for providing a first puff containing an amount of a first vaporizable material and a second puff containing an amount of a second vaporizable material. The first vaporizable material includes a first substance and the second vaporizable material does not include the first substance. The method further includes providing a plurality of puffs from a vaporizer. The plurality of puffs based on the delivery pattern and including the first puff and the second puff. The method further includes receiving user feedback associated with the delivery pattern in response to the providing. The method further includes modifying the delivery pattern based on the user feedback.

In another aspect, a vaporizer includes at least one processor. The vaporizer further includes at least one memory storing instructions which, when executed by the at least one processor, cause the vaporizer to perform operations including determining a delivery pattern for providing a first puff containing an amount of a first vaporizable material and a second puff containing an amount of a second vaporizable material. The first vaporizable material includes a first substance and the second vaporizable material does not include the first substance. The operations further include providing a plurality of puffs from a vaporizer. The plurality of puffs based on the delivery pattern and including the first puff and the second puff. The operations further include receiving user feedback associated with the delivery pattern in response to the providing and modifying the delivery pattern based on user feedback.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g., the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to electronic vaporizer apparatuses, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
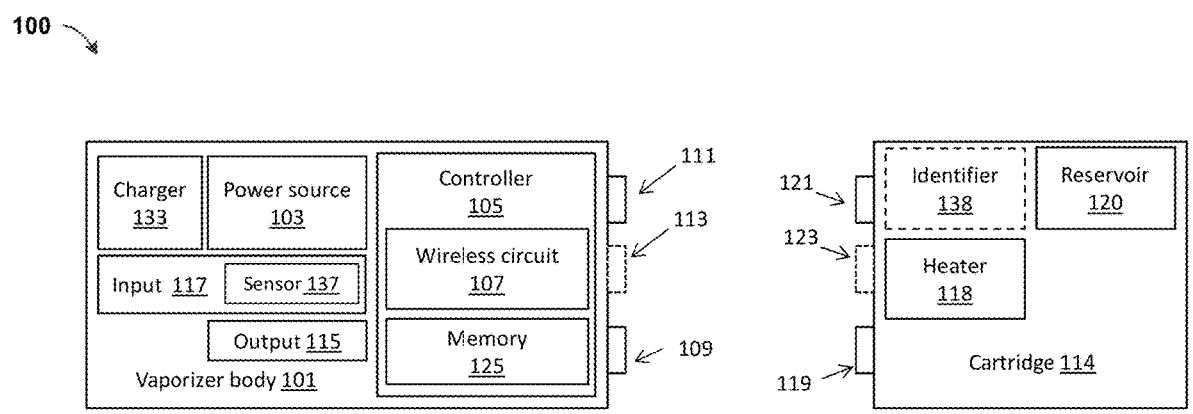
FIG. 1 illustrates a block diagram of a vaporizer, in accordance with some example implementations.

Implementations of the current subject matter include methods, devices, apparatuses, articles of manufacture, and systems relating to vaporizing and/or aerosolizing one or more materials for inhalation by a user. Example implementations include vaporizer devices and systems including vaporizer devices. The term "vaporizer" is used generically in the following description and claims to refer to any of a self-contained apparatus, an apparatus that includes two or more separable parts (e.g., a vaporizer body that includes a battery and/or other hardware, and a cartridge that includes and/or is configured to hold a vaporizable material), and/or the like. A "vaporizer system" as used herein may include one or more components, such as a device in communication (e.g., wirelessly or over a wired connection) with a vaporizer and optionally also the vaporizer itself. A vaporizer or one or more components of a vaporizer system consistent with implementations of the current subject matter may be configured for user control and operation. As used herein, an "aerosol" may refer to a "vapor." Although the term "device" is used herein, the term "apparatus" is intended to be equivalent and should be construed as such.

Examples of vaporizers consistent with implementations of the current subject matter include electronic vaporizers, electronic cigarettes, e-cigarettes, or the like. In general, such vaporizers are hand-held devices that heat (by convection, conduction, radiation, or some combination thereof) a vaporizable material to provide an inhalable dose of the material. The vaporizable material used with a vaporizer may be provided within a cartridge (e.g., a part of the vaporizer that contains the vaporizable material in a reservoir or other container and that can be refillable when empty or disposable in favor of a new cartridge containing additional vaporizable material of a same or different type). A vaporizer may be a cartridge-using vaporizer, a cartridge-less vaporizer, or a multi-use vaporizer capable of use with or without a cartridge. For example, a multi-use vaporizer may include a heating chamber (e.g., an oven) configured to receive a vaporizable material directly in the heating chamber and also to receive a cartridge or other replaceable device having a reservoir, a volume, or the like for at least partially containing a usable amount of vaporizable material. In various implementations, a vaporizer may be configured for use with liquid vaporizable material (e.g., a carrier solution in which an active and/or inactive ingredient(s) are suspended or held in solution or a liquid form of the vaporizable material itself) or a solid vaporizable material. A solid vaporizable material may include a plant material that emits some part of the plant material as the vaporizable material (e.g., such that some part of the plant material remains as waste after the vaporizable material is emitted for inhalation by a user) or optionally can be a solid form of the vaporizable material itself such that all of the solid material can eventually be vaporized for inhalation. A liquid vaporizable material can likewise be capable of being completely vaporized or can include some part of the liquid material that remains after all of the material suitable for inhalation has been consumed.

Nicotine found in cigarettes may become addictive, making it difficult for smokers to quit. Nicotine may provide a level of satisfaction to a user in a number of ways. For example, the user's body may absorb the nicotine and the nicotine may be delivered to the user's brain and the brain's nicotine receptors. The brain may then release one or more of a variety of neurotransmitters, such as dopamine to signal a pleasurable experience. Further, nicotine may create associations with actions or sensations occurring at or around the same time as nicotine intake. Another stimulus occurring temporarily at the same time may become associated with nicotine and the user may become addicted to that stimulus as well as the addictive substance (e.g., nicotine). For example, the sensation of vapor or smoke hitting the back of the throat may itself become addictive and may influence an ability of the user to quit smoking. Additionally, during attempts to quit smoking, nicotine withdrawal may cause anxiety and stress to the user, both of which may be powerful incentives to take up smoking again.

Pharmaceutically approved cessation products such as nicotine patches have a relatively low success rate. For example, a Cochrane Review showed that smokers had a cessation success rate of approximately 4% when unassisted, which was elevated to 6% when nicotine patches were used. Notably, some supportive technologies may increase the success rate of nicotine patches to approximately 20%. However, these approaches, which may involve counseling sessions, may be expensive and beyond the logistical capabilities of most health plans due to the human involvement required. Furthermore, even for the highest success rate using the above techniques, 4 out of 5 smokers do not succeed in their attempt to cease smoking.

E-cigarettes have been shown to help smokers displace their addiction from combusted cigarettes to e-cigarettes and may offer a harm reduced alternative. In some aspects, nicotine-free e-cigarettes may contain sensory stimulants, such as citric acid. In clinical studies, some smokers have reported success in displacing cigarettes with citric acid. However, for some smokers these nicotine-free products may not be directly substitutable.

Example implementations described herein may beneficially provide a nicotine stimulant and similar non-nicotine sensory stimulants to a user in a blind manner in order to aid in the user gradually reducing/eliminating nicotine intake and/or addiction. Additionally, an application and/or a controller may apply machine learning to adjust delivery of nicotine and/or non-nicotine vaporizable material to the user based on received inputs from the user. The inputs may be received directly from the user or they may be learned through monitoring the vaporizer use and behavior of the user.

Consistent with some implementations of the current subject matter, a vaporizer and/or vaporizer system may be configured to identify a vaporizable material to be vaporized, and to adjust the operation of the vaporizer accordingly. For example, a vaporizer may be adapted to receive a cartridge or other pre-loaded container holding a vaporizable material (e.g., a liquid or a solution containing one or more of: nicotine, *cannabis*, citric acid, and/or other active ingredients) and to identify and/or determine information about the vaporizable material and/or the cartridge or other pre-loaded container, such as one or more of: a type of vaporizable material, a concentration of vaporizable material in a solution or other non-pure form of a vaporizable material that is contained in a reservoir or other container of the cartridge, an amount (e.g., a mass, volume, etc.) of vaporizable material in a reservoir or other container of the cartridge, a configuration of the cartridge (e.g., what specific components or types of components such as a heater power or configuration, one or more electrical properties, etc. are present in the cartridge), a lot number of the cartridge, a date of manufacture of the cartridge, an expiration date after which the cartridge should not be used, a manufacture or fill date for the cartridge, or the like.

A vaporizer consistent with implementations of the current subject matter may be configured to connect (e.g., wirelessly or via a wired connection) to a communication device (or optionally two or more devices) in communication with the vaporizer. Such a device can be a component of a vaporizer system as discussed above, and can include first communication hardware, which can establish a wireless communication channel with second communication hardware of the vaporizer. For example, a device used as part of a vaporizer system may include a general purpose computing device (e.g., a smartphone, a tablet, a personal computer, some other portable device such as a smartwatch, or the like) that executes software to produce a user interface for enabling a user of the device to interact with a vaporizer. In other implementations of the current subject matter, such a device used as part of a vaporizer system can be a dedicated piece of hardware such as a remote control or other wireless or wired device having one or more physical or soft (e.g., configurable on a screen or other display device and selectable via user interaction with a touch-sensitive screen or some other input device like a mouse, pointer, trackball, cursor buttons, or the like) interface controls.

A device that is part of a vaporizer system as defined above can be used for any of one or more functions, such as controlling dosing (e.g., dose monitoring, dose setting, dose limiting, user tracking, etc.), controlling sessioning (e.g., session monitoring, session setting, session limiting, user tracking, etc.), controlling nicotine delivery (e.g., switching between nicotine and non-nicotine vaporizable material, adjusting an amount of nicotine delivered, etc.), obtaining locational information (e.g., location of other users, retailer/commercial venue locations, vaping locations, relative or absolute location of the vaporizer itself, etc.), vaporizer personalization (e.g., naming the vaporizer, locking/password protecting the vaporizer, adjusting one or more parental controls, associating the vaporizer with a user group, registering the vaporizer with a manufacturer or warranty maintenance organization, etc.), engaging in social activities (e.g., games, social media communications, interacting with one or more groups, etc.) with other users, or the like. The terms "sessioning", "session", "vaporizer session," or "vapor session," are used generically in the following description and claims to refer to a period devoted to the use of the vaporizer. The period can include a time period, a number of doses, an amount of vaporizable material, and/or the like.

In some implementations of the current subject matter, a vaporizer can include functionality for communicating with a cartridge containing a vaporizable material. The vaporizer may also be in communication with a device that is part of a vaporizer system, although this is not required. The vaporizer, whether under control of or otherwise in communication with a device that is part of a vaporizer system or as a standalone unit separate from a vaporizer system can be configured such that operation of the vaporizer can be modified, controlled, etc. based on one or more parameters that are received from the cartridge or are accessed from a database or other information source based on the identification of the cartridge.

For example, a vaporizer consistent with implementations of the current subject matter can be configured to recognize a cartridge and recite (and in some cases transmit) or otherwise acquire information about the cartridge. In other words, a computing element, such as a controller or the like that is associated with a vaporizer body, can obtain information about the cartridge via some form of data exchange. A variety of methods of cartridge recognition by a vaporizer are within the scope of the current subject matter, including those described in more detail below. Any of the approaches described herein may be performed with or without the addition of wireless communication/connectivity also described herein, although such wireless connectivity as described herein may be advantageously applied, as will be described in greater detail below.

Implementations of the current subject matter also include methods of using a vaporizer and/or a vaporizer system for functions such as determining and/or controlling a dose, amount, or the like of one or more chemical species of the vaporizable material or of the vaporizable material itself. Such determining and/or controlling may be used in conjunction with a nicotine cessation program to improve a likelihood of success in reducing/eliminating nicotine consumption and/or addiction.

Figure 2A:
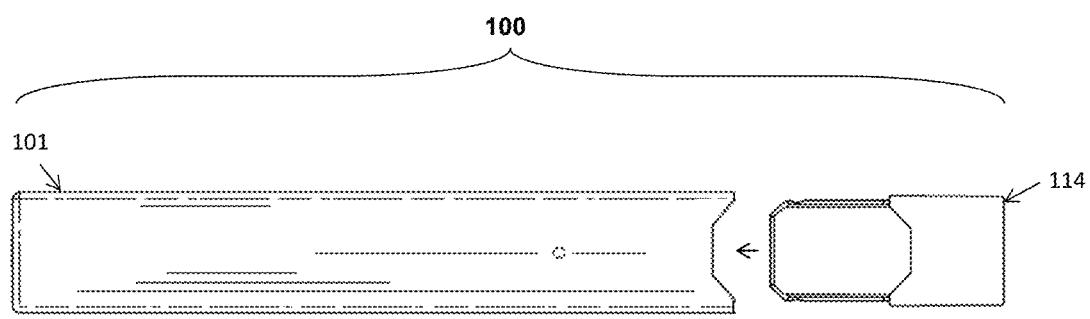
FIG. 2A illustrates an example exploded view of the vaporizer of FIG. 1, in accordance with some example implementations.
Figure 2B:
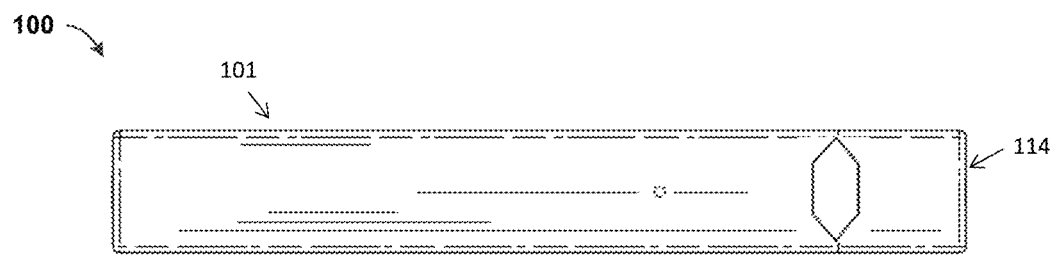
FIG. 2B illustrates another example view of the vaporizer of FIG. 1, in accordance with some example implementations.
Figure 2C:
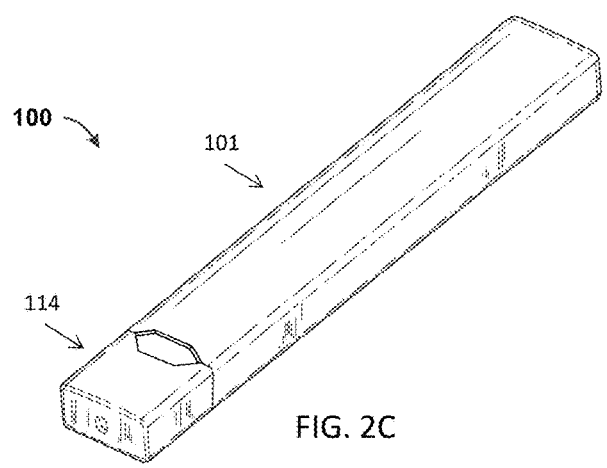
FIG. 2C illustrates another example view of the vaporizer of FIG. 1, in accordance with some example implementations.
Figure 2D:
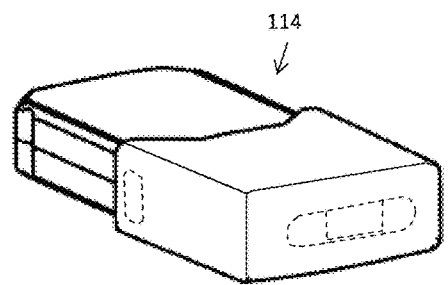
FIG. 2D illustrates an example view of the vaporizer cartridge of FIG. 1, in accordance with some example implementations.

FIG. 1 illustrates a block diagram of a vaporizer 100, in accordance with some example implementations. FIG. 2A illustrates an exploded view of the vaporizer 100 of FIG. 1, in accordance with some example implementations. As illustrated, the vaporizer 100 can include the vaporizer body 101 and the cartridge 114 separated from the vaporizer body 101. FIG. 2B illustrates a (front plan) view of the vaporizer 100 of FIG. 1, in accordance with some example implementations. In some aspects, the vaporizer 100 illustrated in FIG. 2A, when assembled, can look like the vaporizer 100 illustrated in FIG. 2B. FIG. 2C illustrates an example (side perspective) view of the vaporizer 100 of FIG. 1, in accordance with some example implementations. In some aspects, the vaporizer 100 illustrated in FIG. 2A, when assembled, can look like the vaporizer 100 illustrated in FIG. 2C. FIG. 2D illustrates an example view of the vaporizer cartridge 114 of FIG. 1, in accordance with some example implementations. In some implementations, the cartridge 114 can hold and/or be configured to hold a liquid vaporizable material. For example, when a vaporizer includes a cartridge (such as the cartridge 114), the cartridge 114 may include one or more reservoirs 120 of and/or for vaporizable material. Any appropriate vaporizable material may be contained or at least partially contained within the reservoir 120 of the cartridge 114, including solutions of nicotine, citric acid, or other organic materials, solid or semi-solid materials, and/or the like. In an example of a vaporizer cartridge configured for use with solid or semi-sold vaporizable material, the reservoir may include a volume defined at least in part by one or more walls or other structural features of the cartridge sufficient to hold the solid or semi-solid vaporizable material in place before and/or when the cartridge is joined to the vaporizer device.

As illustrated, the vaporizer 100 of in FIG. 1 includes a vaporizer body 101. The vaporizer body 101 may include a housing enclosing a power source 103 (e.g., a device or system that stores electrical energy for on-demand use), which may be a battery, capacitor, a combination thereof, or the like, and which may be rechargeable or non-rechargeable. The housing may also enclose a controller 105, which may include a processor. In the examples shown, a cartridge 114 may be attached on, in, or partially in the vaporizer body 101.

A processor of the controller 105 may include circuitry to control operation of a heater 118, which can optionally include one or more heating elements for vaporizing a vaporizable material contained within the cartridge 114, for example within a reservoir or container that is part of the cartridge 114. In various implementations, the heater 118 may be present in the vaporizer body 101 or within the cartridge 114 (as shown in FIG. 1), or both. The controller circuitry may include one or more clocks (oscillators), charging circuitry, I/O controllers, memory, etc. Alternatively or in addition, the controller circuitry may include circuitry for one or more wireless communication modes, including Bluetooth, near-field communication (NFC), WiFi, ultrasound, ZigBee, RFID, etc. The vaporizer body 101 may also include a memory 125 that may be part of the controller 105 or otherwise in data communication with the controller. The memory 125 may include volatile (e.g., random access memory) and/or non-volatile (e.g., read-only memory, flash memory, solid state storage, a hard drive, other magnetic storage, etc.) memory or data storage.

Further with reference to FIG. 1, a vaporizer 100 may include a charger 133 (and charging circuitry which may be controlled by the controller 105), optionally including an inductive charger and/or a plug-in charger. For example, a universal serial bus (USB) connection may be used to charge the vaporizer 100 and/or to allow communication over a wired connection between a computing device and the controller 105. The charger 133 may charge the onboard power source 103. A vaporizer 100 consistent with implementations of the current subject matter may also include one or more inputs 117, such as buttons, dials, or the like, and/or sensors 137, including accelerometers or other motion sensors, capacitive sensors, flow sensors, or the like. These sensors 137 may be used by the vaporizer 100 to detect user handling and interaction. For example, detection of a rapid movement (such as a shaking motion) of the vaporizer 100 may be interpreted by the controller 105 (e.g., through receipt of a signal from one or more of the sensors 137) as a user command to begin communication with a user device that is part of a vaporizer system and that can be used for controlling one or more operations and/or parameters of the vaporizer 100 as described in more detail below. Additionally or alternatively, detection of a rapid movement (such as a shaking motion) of the vaporizer 100 may be interpreted by the controller 105 (e.g., through receipt of a signal from one or more of the sensors 137) as a user command to cycle through a plurality of temperature settings to which the vaporizable material held within the cartridge 114 is to be heated by action of the heater 118. In some optional variations, detection of removal of the cartridge 114 by the controller 105 (e.g., through receipt of a signal from one or more of the sensors 137) during a cycling-through of the plurality of temperature settings may act to establish the temperature (e.g., when the cycle is at a desired temperature, a user may remove the cartridge 114 to set the desired temperature). The cartridge 114 may then be re-engaged with the vaporizer body 101 by the user to allow use of the vaporizer 100 with the heater controlled by the controller 105 consistent with the selected temperature setting. The plurality of temperature settings may be indicated through one or more indicators on the vaporizer body 101.

A vaporizer consistent with implementations of the current subject matter may also include one or more outputs 115. Outputs 115 as used herein can refer to any of optical (e.g., LEDs, displays, etc.), tactile or haptic (e.g., vibrational, etc.), or sonic (e.g., piezoelectric, etc.) feedback components, or the like, or some combination thereof.

A vaporizer 100 consistent with implementations of the current subject that includes a cartridge 114 may include one or more electrical contacts (such as the electrical contacts 109, 111, 113 shown in FIG. 1) on or within the vaporizer body 101 that may engage complementary contacts 119, 121, 123 (e.g., pins or receptacles) on the cartridge 114 when the cartridge is engaged with the vaporizer body 101. The contacts on the vaporizer body are generally referred to as "vaporizer body contacts" and those on the cartridge are generally referred to as "cartridge contacts." These contacts may be used to provide energy from the power source 103 to the heater 118 in implementations of the current subject matter in which the heater 118 is included in the cartridge 114. For example, when the cartridge contacts and the vaporizer body contacts are respectively engaged by coupling of the cartridge 114 with the vaporizer body 101, an electrical power circuit can be formed allowing control of power flow from the power source 103 in the vaporizer body 101 to the heater 118 in the cartridge 114. A controller 105 in the vaporizer body 101 can regulate this power flow to control a temperature at which the heater 118 heats a vaporizable material contained in the cartridge 114.

Any appropriate electrical contact may be used, including pins (e.g., pogo pins), plates, and the like. In addition, as described below, in some implementations of the current subject matter one-way or two-way communication is provided between the vaporizer body 101 and the cartridge 114 through one or more electrical contacts, which may include the electrical contacts used to provide energy from the power source 103 to the heater 118. The cartridge 114 and the vaporizer body 101 may be removably coupled together, e.g., by engaging a portion of a housing of the cartridge 114 with the vaporizer body 101 and/or the vaporizer housing in a mechanical connection (e.g., a snap and/or friction fit) or the like. Alternatively or additionally, the cartridge 114 and the vaporizer body 101 may be coupled magnetically or via some other coupling or engaging mechanism.

Any of the cartridges described herein may include one or more identifiers 138. The identifier 138 may be recognized, detected, and/or read by the vaporizer body 101, and may convey information about the vaporizable material contained within the cartridge and/or about the cartridge 114 itself. The identifier 138 may include a readable and/or readable/writable cartridge memory. The identifier 138 may include circuitry for receiving and/or transmitting information between the cartridge 114 and the vaporizer body 101. For example, a data exchange circuit may include the cartridge memory, which stores information (e.g., data characterizing one or more parameters of the cartridge), and additional circuitry that forms a data exchange circuit in cooperation with other circuitry on a vaporizer body 101 when the cartridge 114 is coupled to the vaporizer body 101.

In some implementations of the current subject matter, the identifier 138 is passive and may include codes or markings (e.g., bar codes, quick response (QR) codes, etc.). In some examples, the identifier 138 may be structural (e.g., one or more pins, projections, etc.) on the cartridge 114 that may be detected by the vaporizer body 101. Visual or mechanical identifiers may be identified directly by the vaporizer body 101 using an imaging device (e.g., camera, etc.) or reading device (e.g., optical reading) integrated into the vaporizer body (not shown in FIG. 1), or via communication through a separate device, such as a smartphone. For example, a user may take an image of the identifier 138 (e.g., code, marking, etc.) and transmit the code or information derived from the code (such as the information about the vaporizable material and/or the cartridge) to the vaporizer body 101 via wireless circuitry 107, or optionally over a wired connection. A wireless connection (e.g., a wireless communication channel) can be established between first communication hardware of the device and second communication hardware of the vaporizer. The first and second communication hardware can respectively include transceivers for use with one or more wireless communication protocols, non-limiting examples of which are described below.

Figure 3:
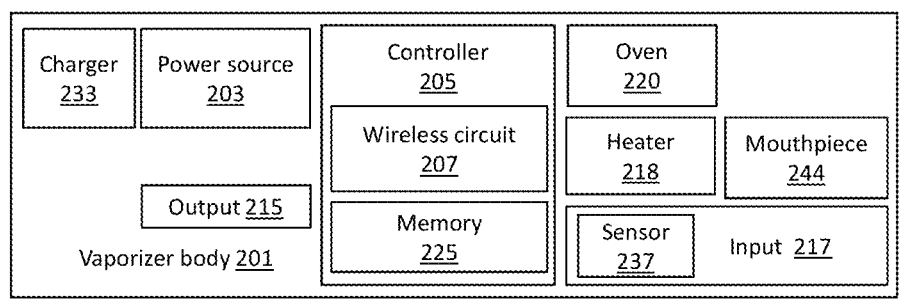
FIG. 3 illustrates a bock diagram of another vaporizer, in accordance with some example implementations.

FIG. 3 shows a schematic diagram of a vaporizer 200 that does not use a cartridge (but may still optionally accept a cartridge), but may instead use a loose-leaf material. The vaporizer 200 in FIG. 3 may include loose vaporizable material that may be placed in an oven 220 (e.g., vaporization chamber). Many of the same elements present in the vaporizer 100 using cartridge 114 shown in FIG. 1 and FIGS. 2A-D may also be included as part of a vaporizer 200 that does not use cartridges. For example, a cartridge-free vaporizer 200 may include a vaporizer body 201 with control circuitry 205 which may include power control circuitry, and/or wireless circuitry 207, and/or memory 225. A power source 203 (e.g., battery, capacitor, etc.) may be charged by a charger 233 (and may include charging control circuitry, not shown). The vaporizer 200 may also include one or more outputs 215 and one or more inputs 217 with sensors 237. In addition, the vaporizer 200 may include one or more heaters 218 that heat an oven 220 or other heating chamber. The heater 218 may be controlled using the resistance of the heater 218 to determine the temperature of the heater, e.g., by using the temperature coefficient of resistivity for the heater. A mouthpiece 244 may also be included.

Figure 4A:
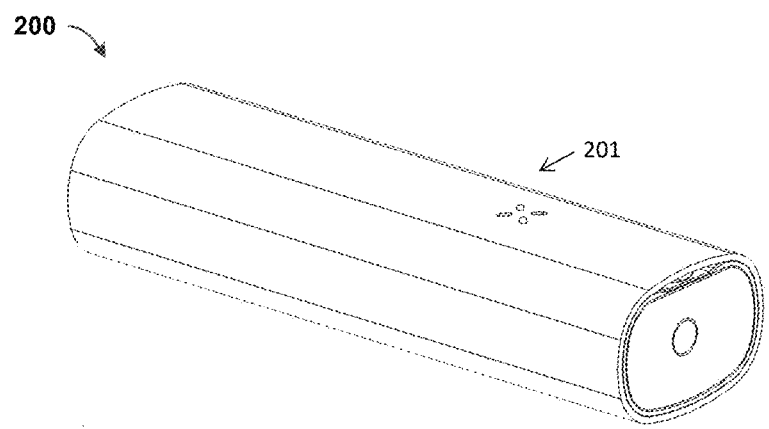
FIG. 4A illustrates an example view of the vaporizer of FIG. 3, in accordance with some example implementations.
Figure 4B:
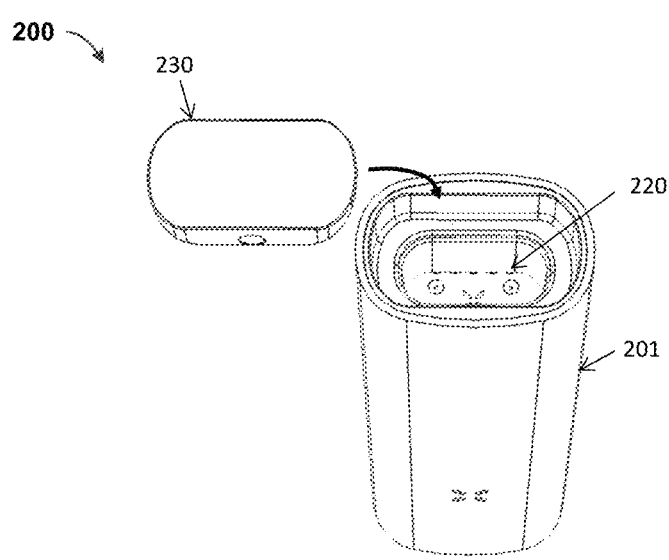
FIG. 4B illustrates another example view of the vaporizer of FIG. 3, in accordance with some example implementations.

FIG. 4A shows a side perspective of an exemplary vaporizer device 200 with a vaporizer body 201. In the bottom perspective view of FIG. 4B, a lid 230 is shown removed from the vaporizer body 201, exposing the oven/vaporization chamber 220.

Figure 5:
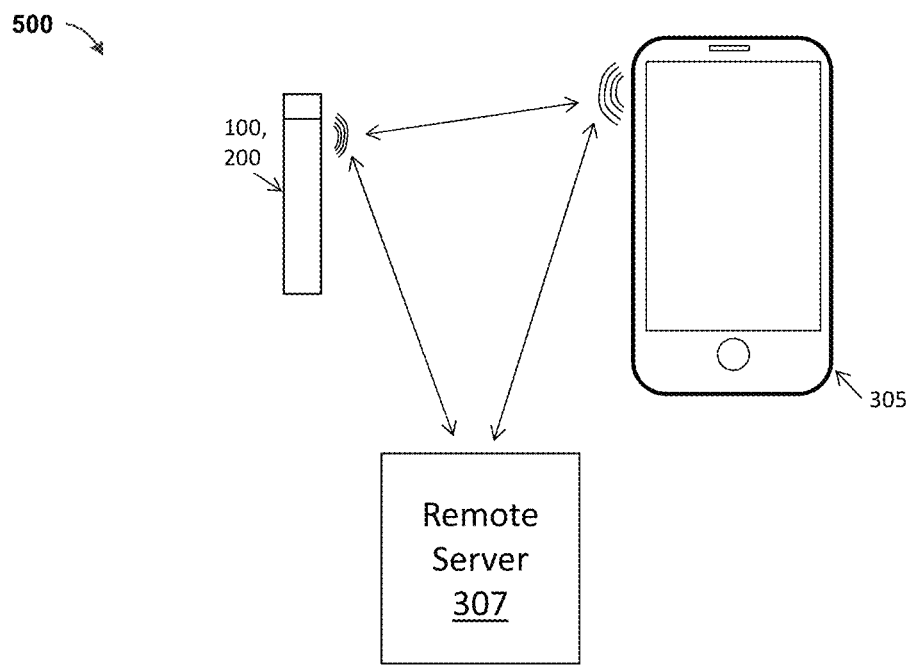
FIG. 5 illustrates a block diagram of communication exchange among a vaporizer, a user device, and a server, in accordance with some example implementations.

FIG. 5 shows a schematic representation of communication among a vaporizer 100, 200, a digital device 305 that wirelessly communicates with the vaporizer 100, 200 and a remote server 307 that may communicate directly with the vaporizer 100, 200, or through the digital device 305. The digital device 305 may be a hand-held mobile device such as a smartphone, smartwatch, tablet, etc., or a desktop or laptop computing device. As noted above, the digital device 305 may optionally be a dedicated remote control device.

In general, as illustrated schematically in FIG. 5, any of the vaporizer apparatuses described herein (such as the vaporizer 100, 200) may remotely communicate with a remote server 307 and/or a digital device 305 such as a wearable electronics device (e.g., Google Glass, smartwatch, smartwear, etc.) and/or a smartphone, smartwatch, etc. Thus, any of these vaporizers 100, 200 may include a communications interface (wireless circuitry 107, 207) that may be implemented through a communication chip (e.g., second communication hardware) in or on the vaporizer 100, 200. Exemplary wireless chips may include, but are not limited to, a Bluetooth chip, such as Parani BCD 210 or Texas Instruments (TI) CC2650 Bluetooth Single-Chip Solution, an NFC-enabled chip (such as Qualcomm's QCA1990), that allows for NFC communication, or enhanced Wi-Fi or Bluetooth communication where NFC is used for link setup. As will be described in detail below, one or more of these wireless circuits may be used for communication with or between the cartridge 114 in implementations that are configured for reading a cartridge 114 as schematically shown in FIG. 1. For example, NFC may be used to read an identifier 138 (as RFID tag) on the cartridge 114.

A wireless communication chip may include a Wi-Fi-enabled chip, such as TI's SimpleLink family's CC3000, that can hook the apparatus to Wi-Fi networks. In some implementations, the wireless circuit comprises a subscriber identity module (SIM) card on board of the vaporizer, a Nano-SIM card, or the like (e.g., allowing 3G/4G cellular network communication). Alternative forms of communication may be used to establish two-way communication between a vaporizer 100, 200 and a user device 305.

Connection between the vaporizer 100, 200 and the user device 305 may be automatic (after an initial set-up) or may be initiated by the user through various settings or may be initiated by shaking the vaporizer 100, 200.

As mentioned above, any of the vaporizer apparatuses described herein that include a cartridge may be configured to recognize and/or identify the cartridge. One or more recognition/identification approaches may be used. The vaporizer may determine information about the cartridge and/or the vaporizable material held in the cartridge, such as one or more of: the type of vaporizable material (e.g., nicotine, *cannabis*, etc.), the concentration of vaporizable material, the amount of vaporizable material, the configuration of the cartridge (e.g., heater, electrical properties, etc.), the lot number of the cartridge, the date of manufacture of the cartridge, expiration date, etc. This information may be directly encoded on the cartridge or a reference indicator may be provided that the vaporizer (or a processor in communication with the vaporizer) may use as an index to look up some or all of this information, or a combination of reference number and directly encoded material may be provided.

In some implementations of the current subject matter, the cartridge may be recognized and/or identified by the engagement between the cartridge and the vaporizer. The cartridge may be configured to include a keyed interaction with the vaporizer. For example, the shape of cartridge may be detected by the vaporizer. For example, the cartridge may include n pins or protrusions. These pins can be detected by the vaporizer when the cartridge is inserted (e.g., by completing an electrical connection); for n pins, there are $2^n$ possible combinations of markings.

The cartridge may be configured or identified based on an electrical property that the vaporizer can detect based on an electrical connection with the cartridge. For example, the vaporizer may make electrical contact through two or more electrical contacts with the heater and/or additional electrical contacts and may detect a characteristic resistance, inductance, or time response (e.g., time constant, RC time constant, LC circuit resonance, etc.).

In some implementations of the current subject matter, the cartridge may be recognized and/or identified by markings on the cartridge identified by the vaporizer. These markings may be visible or not visible to a user. For example, the cartridge may be marked with a characteristic UV, IR or other wavelength-specific ink that can be detected by the vaporizer, which may include, e.g., an emitter/detector pair specific to the marker(s). For example, markings may include an infrared-scannable barcode located on the cartridge. In some implementations, the markings may be a pattern, such as a QR code, bar code, etc., that indicate information about the cartridge and/or the contents (vaporizable material) of the cartridge. The markings may be symbolic, including alphanumeric. The markings may be 'read' or detected directly by the vaporizer, which may include a camera or other optical detector, or it may be indirectly detected via communication with a second device (e.g., wearable, smartphone, etc.) having a camera or the like. For example, markings on the cartridge may be detected by a smartphone such as the user device 305; the smartphone may identify the marking using an application (e.g., software) on the smartphone to look up one or more properties from a look-up table, or it may directly communicate the marking to the vaporizer that may look up the properties, and/or it may communicate with a remote server that may look up the properties and communicate them to the vaporizer directly or through the smartphone.

In some implementations of the current subject matter, the cartridge may be recognized by RFID (Radio-Frequency identification) technology. RFID markers have been used in a wide array of applications for inventory control. Some RFID technologies use active devices which contain their own power source and others use passive RFID devices that interact with another powered device that causes the transfer of data without reliance on power at the passive device. For example, a cartridge may include one or more RFID chips or components that can be detected and read by a reader on the vaporizer to identify and receive information about the cartridge.

In some implementations of the current subject matter, the cartridge may be recognized and/or identified by communicating with a memory (e.g., EEPROM) on the cartridge through an electrical connection with the vaporizer. In implementations in which the heater is present on the cartridge, such as the exemplary vaporizer shown in FIG. 1, it may be advantageous to use one or more of the electrical connections on the cartridge (e.g., contacts 119, 121, 123) that are also used to power and/or control the heater to communicate with the memory. This may be particularly challenging where the cartridge may engage with the vaporizer in more than one orientation, and/or where the heater is controlled through this same contact, and modulation of the applied/received electrical signals between the cartridge and the vaporizer may modify the control and/or temperature determination of the heater. One or more additional electrical contacts may be used in addition to those controlling the heater. In general, communication between the cartridge and the vaporizer may be one way (e.g., reading information about the cartridge and/or the vaporizable material from the cartridge by the vaporizer) or it may be two-way (e.g., reading information about the cartridge and/or the vaporizable material and writing information about the operation of the device, e.g., number of uses, duration of use, temperature settings, etc.). Information may be written to the cartridge, and this information may be used to derive other information about the cartridge, including the amount of material left in the cartridge, etc.

In general, any of the vaporizers described herein may estimate, measure and/or predict the amount of vapor and/or material (including active ingredients) in the vapor that can be delivered to a user. For example, as described in detail below, the apparatuses described herein may be used to determine and/or control dosing of the vaporizable material. For example, the current subject matter includes vaporizers and methods of using such vaporizers for accurate and controlled dose delivery of an active ingredient in a vaporizable material (e.g., nicotine, citric acid, *cannabis*, and any other active ingredient/drug) based on user specified, medical, switching or cessation needs. Dose control may include display of dosing information per use, per session (e.g., multiple uses within a predetermined time period, such as 1-15 minutes, 1-30 min, within 1-60 min, 1-90 min, 1-120 min, etc.), per day, or other predetermined and/or user-defined time period. Dose control may also include monitoring dosing (e.g., amount of one or more active ingredient delivered by the apparatus). Dosing control may also or alternatively include controlling the operation of the vaporizer based on the amount of one or more active ingredient delivered by the apparatus over time, including alerting a user when a predetermined (user defined, factory-set, or third-party set) amount or threshold is approached (e.g., within 50%, 75%, 80%, 85%, 90%, 95%, 98%, 99%, etc. of the predetermined amount) or exceeded, and/or stopping (locking, disabling, etc.) operation of the apparatus when the predetermined threshold is met or exceeded. Apparatuses that include dosing (dose) control may include internal logic (circuitry and/or programming, including application-specific integrated circuit (ASIC) logic) for controlling dosing and/or may communicate with an external processor (via a wireless communication link) that performs all or some of the dose control.

Information about the cartridge and/or a vaporizable material held in the cartridge may be particularly helpful in determining dose. For example information such as one or more of: the type of vaporizable material (e.g., nicotine, citric acid, *cannabis*, etc.), the concentration of vaporizable material, the content of the vaporizable material, the amount of vaporizable material, the configuration of the cartridge (e.g., heater, electrical properties, etc.), the lot number of the cartridge, the date of manufacture of the cartridge, expiration date, the thermal properties of the vaporizable material, etc. may be used to accurately estimate dose. In some implementations of the current subject matter, dose and/or use information may be stored (written) on the cartridge (e.g., in a memory).

Vaporizers, vaporizer systems, and methods of using them for user-customization of device settings and drug usage based on activity patterns are also within the scope of the current subject matter. A vaporizers and/or vaporizer system consistent with the current description may allow a user to personalize a vaporizer and engage in social activities.

A vaporizer and/or vaporizer system consistent with implementations of the current subject matter may be configured to facilitate social interaction through the vaporizer. For example, a vaporizer may be configured to share usage information with others, such as third parties, e.g., health care providers, including doctors, etc. for better prescription and administration of medical treatment. A vaporizer and/or vaporizer system may also be configured to communicate with non-medical third parties (e.g., friends, colleagues, etc.), and with unknown third parties (making some or all information publically available). In some implementations, the vaporizers described herein, either by themselves or in communication with one or more communications devices that are part of a vaporizer system, may identify and provide information about the operation, status or user input from the vaporizer to a public or private network. In some implementations of the current subject matter, a vaporizer and/or vaporizer system may be configured to provide one or more interactive games for use by the user and/or multiple users of different (or the same) vaporizers, including multi-player games that may be used with multiple different vaporizers. Games may be tied to the operation of the vaporizer and/or a user's manipulation of the vaporizer (e.g., based on accelerometer output, touch or lip sensing, draw detection, etc.).

A vaporizer and/or vaporizer system consistent with implementations of the current subject matter may also be configured to provide location information, possibly including one or more of information about user location in proximity to one or more of: other users (known or unknown users, specified or unspecified users, etc.), retailers, specific locations (lounges, clubs, vaporizer-friendly locations), etc. A vaporizer and/or vaporizer system may also be configured to facilitate the placing of orders based on use or operation of the vaporizer and/or vaporizer system.

A vaporizer may include a GPS capability or may access GPS information from another device in communication with the vaporizer as part of a vaporizer system.

As will be described herein in greater detail, a vaporizer may be connected to (e.g., in communication with) an additional (e.g., portable, wearable, smartphone, desktop, laptop, etc.) device, which may enable user programmable dose control, real-time usage monitoring, personalized use settings, device lockout and social features.

Cartridge Recognition.

In general, a vaporizer may include one or more techniques for cartridge recognition and/or communication, including the use of a marker (e.g., QR code, IR or US marker, etc.), mechanical and/or electronic keying, or the like. In general, cartridge recognition is described in U.S. patent application Ser. No. 15/605,890, filed on May 25, 2017, and herein incorporated by reference in its entirety. In particular described herein are methods and apparatuses for electronic cartridge recognition and communication, in which the cartridge may electronically communicate, via one-way or in some implementations two-way (including duplex or multiplex) transmission of information, between a cartridge and the vaporizer so that information may be received by the vaporizer from the cartridge. This information may include information about the vaporizable material and/or the cartridge, such as one or more of: type of vaporizable material, concentration of vaporizable material, amount of vaporizable material, volume of the vaporizable material, properties of the vaporizable material (e.g., thermal properties, composition, etc.), configuration of the cartridge (e.g., heater, electrical properties, etc.), lot number, date of manufacture, expiration date, identity verification for the cartridge, and the like.

In some implementations, the vaporizer may write usage information to the cartridge's memory; usage information can be used to estimate the amount of vaporizable material that has been removed from the cartridge and the amount of vaporizable material remaining. Usage information may include number of puffs/draws, the dosage delivered, or the like. A puff, as the term is generally used (and also used herein) refers to inhalation by the user in a manner that causes a volume of air to be drawn into the vaporizer device such that the inhalable aerosol is generated by combination of vaporized vaporizable material with the air. The inhalable aerosol may be delivered to the user along an airflow path in response to the user drawing/puffing on a mouthpiece of the vaporizer such as mouthpiece 244.

Application/Connectivity.

A vaporizer and/or vaporizer system may include software, firmware or hardware that is separate or separable from the vaporizer and that wirelessly communicates with the vaporizer. In general, application/connectivity is described in U.S. patent application Ser. No. 15/605,890, filed on May 25, 2017, and herein incorporated by reference in its entirety.

For example, applications ("apps") may be executed on a processor of a portable and/or wearable device, including smartphones, smartwatches, and the like, which may be referred to as a personal digital device or optionally just a device (e.g., user device 305 in FIG. 3) that is part of a vaporizer system. These digital devices may provide an interface for the user to engage and interact with functions related to the vaporizer, including communication of data to and from the vaporizer to the digital device or the like and/or additional third party processor (e.g., servers such as the remote server 307 in FIG. 3). For example, a user may control some aspects of the vaporizer (temperature, dosage, etc.) and/or data transmission and data receiving to and from vaporizer, optionally over a wireless communication channel between first communication hardware of the device and second communication hardware of the vaporizer. Data may be communicated in response to one or more actions of the user (e.g., including interactions with a user interface displayed on the device), and/or as a background operation such that the user does not have to initiate or authorize the data communication process.

User interfaces may be deployed on a digital device and may aid the user in operating the vaporizer. For example, the user interface operating on a digital device may include icons and text elements that may inform the user of various ways that vaporizer settings can be adjusted or configured by the user. In this manner (or in others consistent with the current subject matter) information about a vaporizer can be presented using a user interface displayed by the communication device. Icons and/or text elements may be provided to allow a user to see information about vaporizer status, such as battery information (charge remaining, vapor draws remaining, time to charge, charging, etc.), cartridge status (e.g., type of cartridge and vaporizable material, fill status of cartridge, etc.), and similar device status. Icons and/or text elements may be provided to allow a user to update internal software (a.k.a., firmware) in the vaporizer. Icons and text elements may be provided to allow a user to set security and/or authorization features of vaporizer, such as setting a PIN code to activate the device or the use of personal biometric information as a means of authentication. Icons and text elements may be provided to allow a user to configure foreground data sharing and related settings.

A vaporizer can interface (e.g., communicate) with digital consumer technology products and with apps as a way of relaying information and data to add additional functionality.

Cartridge-related settings of the vaporizer can be based on information about the cartridge, including liquid components and/or formulation, or similar such that the information relating to the liquid may be vaporized or aerosolized. The liquid related settings of the vaporizer can have predetermined as well as user configurable settings to modulate, configure, adjust or otherwise configure the device activation parameters.

A vaporizer may be configured (programmed) with time based settings, such as for example, user specific temporal configurations such as the user preferring higher active component delivery per inhalation at specific times of the day. A vaporizer can be configured such that the vaporizer delivers dosages of an active component based on the time of day. For example, the vaporizer can be configured such that the dosage delivered to the user is highest, or at maximum value (or similar) in the evening and is held at a lower delivered dose per inhalation, or minimum value (or similar) earlier in the day. The user can program these settings (and others described herein) based on personal preference.

Taste and/or flavor related settings of the vaporizer can minimize, maximize, and or modulate functional effects of the taste and/or flavor component of the vapor product. For example, the vaporizer can be configured to activate in such a way that the flavor delivered from the vapor or aerosol is minimized, maximized, or modulated over the period of an inhalation. Some components of the liquid being vaporized that may contribute to the flavor characteristics of the vapor or aerosol may be more profound, more prevalent, or more substantial when the vaporizer is activated with higher temperature ranges being generated by the heating element than when lower temperature ranges are being generated by the heating element (within the range of temperatures that the heating element may operate in order to generate a vapor or aerosol for inhalation by the user). For example, the user may set the vaporizer to perform for maximal, minimal, moderate, or another interim value of flavor for the vapor or aerosol product. The vaporizer may modulate the heating element activation cycle accordingly.

Functional effect-related setting of the vaporizer can minimize, maximize, or modulate the functional effects related to pharmacodynamics and pharmacokinetics of an active ingredient or drug component of the vapor or aerosol product. For example, the vaporizer can be configured to activate in such a way that the active component or drug delivered from the vapor or aerosol is minimized or maximized in terms of target tissue or organ delivery. Particle size may be modulated. A user may be using a vaporizer for the delivery of nicotine as the active or drug component in the vapor or aerosol. It may be desirable for (or by) the user to have an option for more rapid delivery of the nicotine to the bloodstream—such as after a period of not having nicotine (when the user's urge or craving is likely to be elevated). Alternatively, at times it may be desirable for (or by) the user to have a slower absorption of nicotine into the blood stream such as at times when: (i) the user's craving or urge is low, (ii) when the user wants to have a more prolonged period of time before they have the urge or craving for nicotine—such as prior to going to sleep, or an event where they will be unable to use the device for dosing or administration of the nicotine. The vaporizer settings relating to the activation of the device and the temperature of the heating element and heating element activation characteristics may be modulated such that, for example, at lower temperature activation the particle size of the drug component is larger than at times of a higher temperature activation of the heating element. Thus, by modulating the input of thermal or heat energy inputted into the vaporization chamber by the heating element to volatize or vaporize the liquid containing the active component(s) or drug(s), the characteristics of the vapor or aerosol in relation to the particle size of the active component(s) or drug(s) can be wholly or partially modulated by the user. These settings can also be used by the end user or healthcare provider (or similar) to reduce dependence on the active component(s) or drug(s) such as nicotine. This transition can also be used in conjunction with nicotine dosage reduction for reducing or mitigating the user's nicotine dependence or addiction.

An app may receive alerts and notifications associated with the vaporizer. These alerts and notifications can include, for example: battery life status, battery condition data (such as number of battery cycles), and battery "health" (such that the user can be notified, as desired, to the current and "real time" overall condition of the vaporizer internal battery(ies)).

A vaporizer and/or an associated application (app) running on a digital consumer technology product (e.g., a device that forms or is part of a vaporizer system as described above) may share data with a manufacturer, manufacturer affiliate, or other entity (retailer, healthcare provider, supplier, marketing entity, etc.). A vaporizer and/or an associated application may gather, receive, log, store, transmit, extrapolate, and/or the like, anonymous or user specific usage data—such as frequency of use. A vaporizer and/or an associated application can gather, receive, log, store, transmit, extrapolate, and/or the like, user specific usage data such as activation cycle characteristics, such as duration of activations and user specified activation settings (if applicable.) A vaporizer and/or an associated application can gather, receive, log, store, transmit, extrapolate, and/or the like, user specific demographic information. A vaporizer and/or an associated application can gather, receive, log, store, transmit, extrapolate, and/or the like, user specific socioeconomic information. A vaporizer and/or an associated application can gather, receive, log, store, transmit, extrapolate, and/or the like, user specific information. A vaporizer and/or an associated application can gather, receive, log, store, transmit, extrapolate, and/or the like, user specific feedback information. A vaporizer and/or an associated application can gather, receive, log, store, transmit, extrapolate, and/or the like, user specific demographic information. A vaporizer and/or an associated application can gather, receive, log, store, transmit, extrapolate, and/or the like, user specific feedback information using surveys, polls, and the like, and/or data analytics.

A vaporizer and/or an associated application can gather, receive, log, store, transmit, extrapolate, and/or the like, anonymous and/or user specific usage and/or reliability data such as device errors or malfunctions. A vaporizer and/or an associated application can gather, receive, log, store, transmit, extrapolate, and/or the like, user specific usage and/or reliability data such as requests for warranty services, repairs, and or replacements, etc. A vaporizer and/or an associated application can gather, receive, log, store, transmit, extrapolate, and/or the like, user specific customer satisfaction data such as requests for technical support. A vaporizer and/or an associated application can gather, receive, log, store, transmit, extrapolate, and/or the like, user specific sales lead data such as requests for product information. A vaporizer and/or an associated application can gather, receive, log, store, transmit, extrapolate, and/or the like, user specific usability data such as requests for usage instructions. A vaporizer and/or an associated application can gather, receive, log, store, transmit, extrapolate, and/or the like, user specific information such as requests for information on product features or functions. A vaporizer and/or an associated application can gather, receive, log, store, transmit, extrapolate, and/or the like, user specific marketing data such as requests for information on purchasing a vaporizer and/or acquiring a vaporizer by way of a prescription from a physician or healthcare provider.

A vaporizer, via an associated application running on a device that is part of a vaporizer system, can gather, receive, log, store, transmit, extrapolate, data share, and/or the like, data from a network that may be used to identify, contact, or connect with other users of vaporizers, and may, via an associated application, gather, receive, log, store, transmit, extrapolate, data share, and/or the like, data from a network that may be used to identify, contact, or connect with other users within the network. The vaporizer may select and/or authorize the sharing of all or some of the data gathered, received, logged, stored, transmitted, extrapolated, shared, or the like by the vaporizer, or gathered directly from the user using applications associated with the vaporizer. A vaporizer may select and/or authorize the sharing, via a network, of all or some of the data gathered, received, logged, stored, transmitted, extrapolated, shared, or the like by the vaporizer, or gathered directly from the user using applications associated with the vaporizer. The network may comprise social media. The social media membership may comprise a user's family. The social media membership may comprise a user's friends. The social media membership may comprise a support group or similar (e.g., quit smoking group). The social media membership may comprise a third-party service, company, organization (e.g., church), other users of the vaporizer, or the like.

A vaporizer and/or an associated application can share data gathered by the vaporizer, or gathered directly from the user using the application with the user's healthcare provider. A vaporizer and/or an associated application can share data gathered by the vaporizer, or gathered directly from the user using the application with the user's healthcare network. A vaporizer and/or an associated application can share data gathered by the vaporizer or gathered directly from the user using the application with the user's insurance provider. A vaporizer and/or an associated application can share data gathered by the vaporizer, or gathered directly from the user using the application with the user's pharmacy and/or prescription drug provider, or the like. A vaporizer and/or an associated application can depersonalize or otherwise make anonymous data gathered by the vaporizer or gathered directly from the user so that the depersonalized data can be shared or used for purposes such as research, analysis, publication, or similar purposes.

A vaporizer and/or an associated application can provide for the notification of the user via the vaporizer and/or the associated application of the availability of a prescription issued or written for the end user being ready for pick-up, delivery, shipment to the user or similar of a prescription component intended for delivery to the patient by a vaporizer. For example, a pharmacy may send a notification to the user, via the vaporizer and/or an associated application, such as to notify the user that their prescription for a vaporizer or vaporizable material (e.g., cartridges or liquids) is available for the user to pick up from the pharmacy (other commercial venues, not limited to pharmacies, may also do this, including shops, dispensaries, etc.). A vaporizer and/or an associated application can allow for healthcare providers, networks, agents, authorized third parties or similar entities to send alerts, messages, surveys, or similar to the user via the vaporizer and/or the associated application. A vaporizer and/or an associated application can allow for healthcare providers, networks, agents, authorized third parties or similar entities to access data that is generated as a result of surveys, or similar through the vaporizer and/or the associated application.

A vaporizer and/or an associated application can authorize (e.g., allow) a healthcare provider to configure, adjust, modulate, and/or manipulate vaporizer settings. A vaporizer and/or an associated application can authorize a healthcare provider to configure, adjust, modulate, and/or manipulate vaporizer settings which the user is not authorized to change, alter, reconfigure or change the settings, configurations, etc. made by the healthcare provider. A vaporizer and/or an associated application can authorize a representative or agent of the healthcare provider to configure, adjust, modulate, and/or manipulate vaporizer settings which the user is not authorized to change, alter, reconfigure or change the settings, configurations, etc. made by the representative or agent of the healthcare provider.

A vaporizer and/or an associated application can facilitate, prompt, or the like, a user to rate (such as through common methods such a 1-10 where "10" is the best, or 1-5 "stars" where "5" stars is the best) their vaporizer, vaporizer configurations, cartridge (e.g., particular flavor or brand of cartridges, etc.), or the like. A vaporizer and/or an associated application can facilitate, prompt, or the like, the user to rate other user configurations. A vaporizer and/or an associated application can share and access a database of user configurations that may or may not have ratings and be able to access the user configurations through the application and download user configurations for use in the user's own device. A vaporizer and/or an associated application can have the ability to share and access a database of user configurations that may or may not have ratings and be able to access the user configurations through the application and upload their user configurations for use in other users' devices.

A vaporizer and/or an associated application can include features (e.g., software-based buttons or controls and/or physical input devices or controls) that enable user control of the functionality, features, configurations etc. of a vaporizer and/or an associated application using various features of the application referred to as configurations or settings. In some implementations of the current subject matter, the configurations and/or setting may include a variety of different settings as described in U.S. patent application Ser. No. 15/605,890, filed on May 25, 2017, previously incorporated by reference in its entirety.

The systems, controller, and functions described above may be implemented with or executed by one or more computer systems. The methods described herein may be stored on a computer readable medium.

Dose Control.

A vaporizer and/or vaporizer system may include dose control and/or dose metering. In general, dose control is described in U.S. patent application Ser. No. 14/960,259, filed on Dec. 4, 2015, and herein incorporated by reference in its entirety.

As described above, a vaporizer and/or a device that is part of a vaporizer system as defined above may include a user interface (e.g., including an app or application software) that may be executed on a device in communication, which may be configured to determine, display, enforce and/or meter dosing. For example, a vaporizer may have a "unit dose" mode/indicator that is displayed on the vaporizer and/or an application. The unit dose could be changed by the connected application and/or by directly controlling the vaporizer. For example, a user may want to go from 1 mg nicotine per dose to 2 mg of nicotine per dose.

The dose unit may be programmable. For example, a user may program a dose based on previous (recorded) use; e.g., the user may press a "start" button on the app, take enough puffs until satisfied, and then press "stop" on the app. In addition, the user may input user-specific data that may be helpful in determining and/or metering dosing. For example, the user may input body weight, gender, and any other relevant data. Such info can be used for adjusting dose of therapeutic drugs such as pain killer, sleep aid, etc. accordingly.

As mentioned, in some implementations of the current subject matter, the vaporizer and/or app running on a device that is connected (or connectable) to the vaporizer may record use or operation of the device and may play back this use later. In general, the vaporizer or app may record a first operational parameter (e.g., temperature setting, ramp time to heat, etc.) and a second use parameter (e.g., number of puffs, cumulative dose, use time, etc.), may store the recorded operational parameter and use parameter as a use profile, may associate the recorded use profile with a control, button, icon, etc., and may program the device operation based on the use profile, so that the operational parameter is modified automatically as the actual operational parameter tracks with the recorded operational parameter.

For example, the user may record a use profile including the number of puffs (e.g., draw events, inhalations, etc.) between changes in the temperature, as well as the temperature so that this use profile may be replayed later, e.g., by selecting a button or other indicator associated with the recorded/programmed use profile. In some implementations, the vaporizer and/or app may record the temperature and one or more second use parameters, such as one or more of: puff time (duration), puff count (number of puffs), energy applied to vaporizable material (e.g., cumulative joules of energy), dosage/exposure, etc. Playback may be indexed on any of the recorded use parameters such as the number of puffs, cumulative duration of puffing, cumulative energy applied, cumulative dose, etc. and may set or modify the operational parameter (e.g., applied vaporization temperature, energy applied, etc.) of the vaporizer to the recorded temperature to match the recorded and/or programmed temperature as the vaporizer is operated, so that the same use profile will be followed. For example, a user may record a use profile while operating the device at a first temperature (e.g., 150° C.) for 5 draws (puffs), then increasing the temperature to 180° C. for five more puffs, then increasing the temperature to 200° C. for 10 puffs. The recorded operational profile may be stored on the vaporizer, app, or some other connected memory, and associated with a control (e.g., icon, graphic, text, button, etc.) on the vaporizer, app and/or a remote processor or memory. The recorded operational profile may then be played back, e.g., by selecting an icon (or button, control, text, etc.) on the app or vaporizer that has been associated with the recorded/programmed profile. During playback, the vaporizer may wait until the same or a similar operational parameter (e.g., puffs, time of use, applied power, dose, etc.) is matched or exceeded and may control the heater based on the recorded profile. In the example above, the recorded operational profile may be played back later by pressing the icon; the vaporizer and/or app may compare the use parameter (number of puffs, etc.) to the current operation of the vaporizer and may adjust the operational parameter accordingly to match the use profile.

The use profile may be recorded, or it may be programmed, or both (e.g., a recorded use profile may be modified by a user on the vaporizer and/or app, etc.).

In some examples, dose (e.g., cumulative dose) may be the use parameter that is monitored. In some implementations of the current subject matter, dose may be calculated as described in U.S. patent application Ser. No. 14/960,259, filed on Dec. 4, 2015, previously incorporated by reference in its entirety. The cumulative dose may be stored for transmission and/or display. Further, the dose may be used to control operation of the vaporizer.

In one example of a nicotine dose control, the user could set a target cap for how much nicotine he/she wants in a day. In some implementations, the device won't lock the user out from having more, but it will notify if a target has been exceeded. Alternatively, the device may lock the user out.

In an example of THC dose regulation, the dose control may allow a user to treat symptoms without having too much psychoactive effect. For example, usage data can be shared with a doctor to allow for better prescription/administration. In general, for medical use, the vaporizer or app can correlate dose with logged symptoms. Alternatively or additionally, for recreational use, the vaporizer or app may allow a user to more easily figure out the right amount for them and then repeatedly deliver that dose.

In some implementations of the current subject matter, the application or vaporizer may inform the users of the driving under the influence (DUI) limit of THC in their state and set warning/alert when one time usage exceeds the limit based on estimated blood level (e.g., 5 ng/mL blood level in Colorado or 3.5-5 ng/mL blood level according to this report http://www.canorml.org/healthfacts/DUICreport.2005.pdf). The vaporizer or app may also include a table similar to the number of drinks vs. blood alcohol content (BAC) table included in department of motor vehicles (DMV) letters. The vaporizer and/or app may alternatively or additionally estimate blood THC concentration based on the user's body weight and gender info.

Monitoring—Health and Cessation.

A vaporizer and/or applications running on a device that is part of a vaporizer system consistent with implementations of the current subject matter may also be configured to monitor usage for a digital health regimen, and/or smoking cessation, etc. For example, similar to weight loss monitoring devices, a vaporizer or an app or both may be useful for people who want to reduce nicotine consumption, and/or keep track of how much consumed within a certain amount of time. For example, the vaporizer and/or app may be configured to allow cigarette-e-cigarette dual users to log in how many cigarettes they consume and compare the total amount of HPHCs and nicotine they get on different days when they use different combinations.

Figure 6:
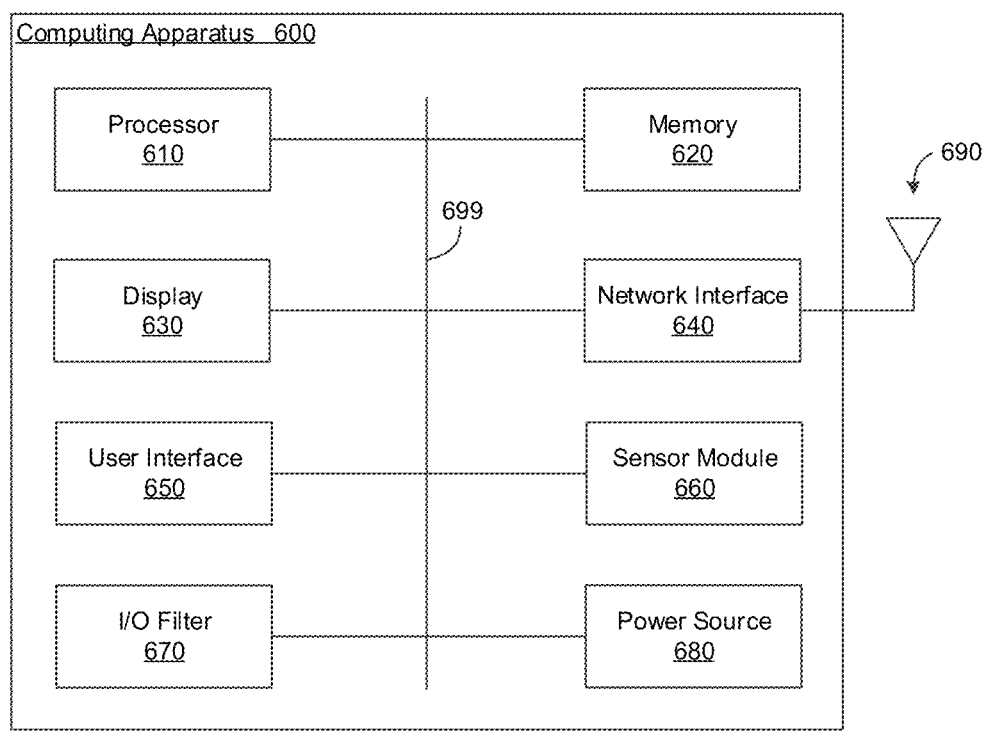
FIG. 6 illustrates an example device which may be used to implement one or more of the described features and/or components, in accordance with some example implementations.

FIG. 6 illustrates an example computing apparatus 600 which may be used to implement one or more of the described features and/or components, in accordance with some example implementations. For example, at least a portion of the computing apparatus 600 may be used to implement at least a portion of the vaporizer 100, the vaporizer 200, the user device 305, the remote server 307, and/or like. The components of the computing apparatus 600 can be implemented in addition to or alternatively from any of the components of the vaporizer apparatuses 100, 200 illustrated and/or described.

The computing apparatus 600 may perform one or more of the processes described herein. For example, the computing apparatus 600 may be used to execute an application providing for user control of a vaporizer in communication with the computing apparatus 600 and/or to provide an interface for the user to engage and interact with functions related to the vaporizer, in accordance with some example implementations.

As illustrated, the computing apparatus 600 may include one or more processors such as processor 610 to execute instructions that may implement operations consistent with those described herein. The computing apparatus 600 may include memory 620 to store executable instructions and/or information. Memory 620 may include solid-state memory, solid-state disk drives, magnetic disk drives, or any other information storage device. The computing apparatus 600 may include a network interface 640 to a wired network or a wireless network, such as the network described with reference to FIG. 5. In order to effectuate wireless communications, the network interface 640, for example, may utilize one or more antennas, such as antenna 690.

The computing apparatus 600 may include one or more user interfaces, such as user interface 650. The user interface 650 can include hardware or software interfaces, such as a keyboard, mouse, or other interface, some of which may include a touchscreen integrated with a display 630. The display 630 may be used to display information, such as information related to the functions of a vaporizer, provide prompts to a user, receive user input, and/or the like. In various implementations, the user interface 650 can include one or more peripheral devices and/or the user interface 650 may be configured to communicate with these peripheral devices.

In some aspects, the user interface 650 may include one or more sensors and/or may include an interface to one or more sensors, such as those described herein. The operation of these sensors may be controlled, at least in part, by a sensor module 660. The computing apparatus 600 may comprise an input and output filter 670, which can filter information received from the sensors or other user interfaces, received and/or transmitted via the network interface 640, and/or the like. For example, signals detected through the sensors can be passed through the filter 670 for proper signal conditioning, and the filtered data may then be passed to the sensor module 660 and/or processor 610 for validation and processing (e.g., before transmitting results or an indication via the network interface 640). The computing apparatus 600 may be powered through the use of one or more power sources, such as power source 680. As illustrated, one or more of the components of the computing apparatus 600 may communicate and/or receive power through a system bus 699.

Implementations described herein may incorporate a system for cessation or reduction of nicotine and/or smoking dependency and/or treatment of withdrawal symptoms. Similar systems may also facilitate a reduction of harm in switching from cigarettes to non-combusted nicotine use.

For example, the cessation system may include a vaporizer and/or vaporizer system that has more than one reservoir 120 and/or vaporization chamber 220. A first reservoir 120 may hold a non-nicotine or a reduced nicotine vaporizable material, such as citric acid, capsaicin, and/or the like. A second reservoir(s) 120 may hold a chamber vaporizable material that includes a non-zero percentage of nicotine. Similarly, a vaporization chamber 220 may generate a non-nicotine and/or a reduced nicotine inhalable vapor. In some aspects, a second vaporization chamber 220 may generate a nicotine-containing inhalable vapor. The nicotine-containing inhalable vapor may include a higher percentage of nicotine than the non-nicotine or the reduced nicotine inhalable vapor.

In some aspects, the cessation system may include a single reservoir 120 and/or vaporization chamber 220. For example, the cessation system may include a series of pods/cartridges of different nicotine concentrations. Cartridges with lower nicotine concentration may have a higher citric acid, or other non-nicotine sensory agent, concentration than cartridges with a higher nicotine concentration. The concentration of nicotine may be sufficient to protonate the nicotine, in order to achieve a similar back of the throat sensation when inhaling a vapor from lower nicotine concentration cartridges (e.g., <3% nicotine or lower concentration than a higher concentration cartridge). The non-nicotine and/or the reduced nicotine vaporizable material may be configured to create sensations which mimic at least some of the sensorial properties of inhaling nicotine, or higher concentrations of nicotine. The non-nicotine and/or the reduced nicotine vaporizable material may also include any non-nicotine or reduced-nicotine containing e-liquid.

The vaporizer and/or vaporizer system may be configured to toggle, on a puff by puff basis, between nicotine and non-nicotine puffs. In some aspects, the vaporizer and/or vaporizer system may also be configured to dynamically mix of non-nicotine vaporizable material (e.g., citric acid) with the nicotine-containing vaporizable material to adjust a nicotine ratio/concentration in the inhalable vapor. In some implementations, the controller 105, 205, a connected application (e.g., an app on the user device 305 and/or in the cloud), and/or the processor 610 may be configured to toggle between reservoirs and/or chambers and/or mix the different nicotine concentration vaporizable material. This toggling and/or mixing may beneficially allow the vaporizer and/or vaporizer system to control a concentration of nicotine in each puff of the user. The vaporizer and/or vaporizer system may utilize adaptive behavioral approaches, such as machine learning, to select an optimized pattern of nicotine vs. non-nicotine puffs.

Figure 7:
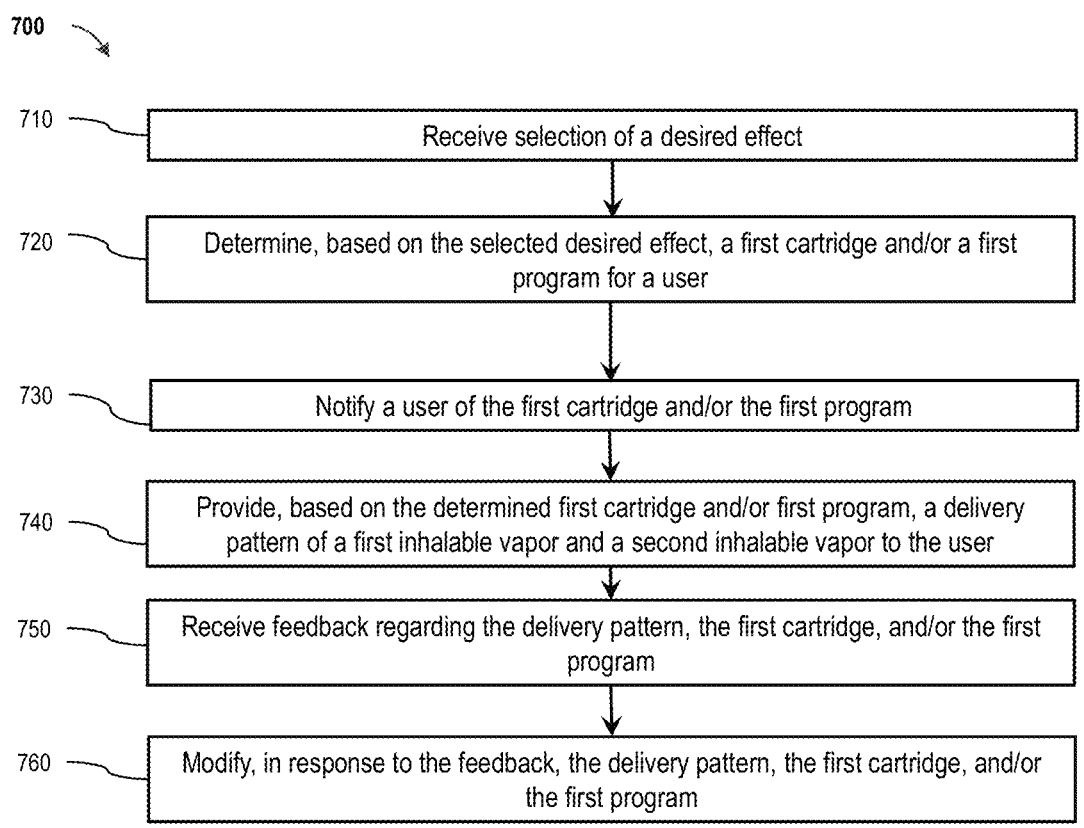
FIG. 7 illustrates a flowchart of a method for nicotine cessation, in accordance with some example implementations.

FIG. 7 illustrates a flowchart of a method 700 for nicotine cessation, in accordance with some example implementations. In some implementations, the method 700 (or at least a portion thereof) may be performed by one or more of the vaporizer 100, the vaporizer 200, the user access device 305, the remote server 307, the computing apparatus 600, other related apparatuses, and/or some portion thereof.

The method 700 may optionally include some or all of the following. At 710, the cessation system may receive a selection of a desired effect. The received selection may be a user selection from the user access device 305 running an app. The desired effect may include quitting smoking cigarettes, reducing/eliminating nicotine consumption, and/or the like. At 720, the cessation system may determine, based on the selected desired effect, a first cartridge and/or a first program (e.g., a first cessation program) for a user. In some aspects, the first cartridge may include a cartridge that has two or more reservoirs 120. At least one reservoir 120 may hold a nicotine containing vaporizable material and another at least one reservoir 120 may hold a non-nicotine vaporizable material. Additionally, at least one reservoir 120 may hold a nicotine containing vaporizable material with a lower concentration of nicotine than a vaporizable material in another reservoir 120. The first program may include a cessation program tailored to the user.

In some aspects, the cessation program may be determined based on user inputs. For example, the user may download an app which may control an amount and/or level of nicotine (or other substance) that is delivered to the user during use of the vaporizer. The app may initially prompt the user to answer questions about the user and/or the user's desired cessation program. For example, the app may prompt questions regarding about the user's age, height, weight, ethnicity, location, current smoking devices used, current and past smoking/tobacco/nicotine use, current and past vaporizer use, user behavior, length of smoking/tobacco/nicotine use, eating habits, exercise habits, motivation for quitting smoking, personality type, timeline for quitting, a desired reduction in nicotine, flavor preferences, and/or the like. The app may create a user profile based on the user's inputs and/or answers to the questions. Based on the user profile and/or user inputs, the app may generate the first program for the user. The first program may include an amount of nicotine per vaporizer dose and/or vaporizer session, a pattern of providing nicotine vs. non-nicotine (or reduced nicotine) puffs to the user), a time period for reducing/eliminating nicotine (or another substance), a concentration of nicotine in the first cartridge and/or reservoirs 120, a concentration of non-nicotine material (e.g., citric acid) in the first cartridge and/or reservoirs 120, a rate of reduction of nicotine over time, a time of day for nicotine consumption, and/or the like.

At 730, the cessation system may notify the user of the first cartridge and/or the first program. The notification may include an email, text, app message, and/or any other message to indicate to the user that the first cartridge and/or the first program has been determined. The notification may include information on how the user may purchase the first cartridge, how to begin the first program, and/or other information associated with the first cartridge and/or the first program. At 740, the cessation system may provide, based on the determined first cartridge and/or first program, a delivery pattern of a first inhalable vapor (e.g., nicotine containing vapor) and a second inhalable vapor (e.g., non-nicotine or reduced nicotine vapor) to the user. In some implementations, the providing the delivery pattern may include selectively toggling between providing at least one puff of the first inhalable vapor and at least one puff of the second inhalable vapor. In some aspects, the amount, frequency, pattern, volume, time, and/or location of the toggling may be included in the first program and/or first cartridge.

At 750, the cessation system may receive feedback regarding the delivery pattern, the first cartridge, and/or the first program. For example, the user may provide or may be prompted to provide feedback at various points in time during the first program. In some aspects, the user may provide feedback via an app, via a gesture of the vaporizer, a sensor, a selection of an input on the vaporizer and/or user interface 650, via learned behavior from past history, and/or the like. The feedback may include a current level of satisfaction, craving, or desire for a cigarette, a time since last combusted cigarette, a number cigarettes smoked per day, a level of satisfaction after a vaporizer puff, location of cigarette use, an activity that accompanied the cigarette use, whether the user smoked the cigarette alone or in a group, time of day of cigarette use, and/or the like.

At 760, the cessation system may modify, in response to receiving the feedback, the delivery pattern, the first cartridge, and/or the first program. The cessation system may include an adaptive pattern recognition system, such as a machine learning algorithm (e.g., a neural network), that may identify optimal tunings to the first cartridge and/or the first program for the user. The adaptive pattern recognition system may include the controller 105, 205, the processor 610, the app, and/or the vaporizer system. Modifications to the first cartridge and/or the first program may result in the cessation system selecting a second cartridge and/or second program with parameters or characteristics different from the first cartridge and/or the first program. For example, the second cartridge and/or the second program may include different concentrations of nicotine, patterns of nicotine and non-nicotine puffs, time schedules of nicotine use, and/or the like.

The machine learning algorithm may receive a variety of inputs that it may analyze in order to determine the second cartridge and/or second program. For example, the machine learning algorithm may base at least a part of the determination on a time of day, geographic location, user feedback, or other factors. The machine learning algorithm may determine that different vaporizer doses and/or sessions would have different optimal nicotine vs. non-nicotine ordering patterns and/or ratios. For example, at later stages of the cessation program the machine learning algorithm may increase the ratio of citric acid puffs and may determine that first few puffs of vaporizer session are nicotine and then after that citric acid puffs may give the user a similar level of satisfaction.

The machine learning algorithm may also be configured to determine an order in which to provide the nicotine puffs and the non-nicotine/reduced nicotine puffs. For example, the machine learning algorithm may determine that it is important for the first puff in a vaporizing dose or session to contain nicotine, or not. The order/randomness of nicotine vs. non-nicotine puffs may be an optimized variable that is determined and adjusted as the user progresses through the first/second cartridge and/or first/second program.

The moving from one vaporizable material (e.g., nicotine) to another vaporizable material (e.g., citric acid) on a puff-by-puff thing within a session may provide various advantages. For example, a user may inhale a number of the puffs that are full potency of nicotine which may give the user a level of satisfaction that extends psychologically and physiologically through the a future non-nicotine puff so that the user's brain is still responding to the previous nicotine puff. The staying power of the level of satisfaction from one or more nicotine puffs may allow the machine learning algorithm more latitude to schedule more non-nicotine future puffs as opposed to a simple alternating pattern across a consistent number of puffs.

Additionally, the ability to switch vaporizable materials in a way that is blind to the user may provide additional benefits. Blinding which vaporizable material is being delivered may be beneficial to the success of a placebo effect or second order stimulus (e.g., the non-nicotine puff). In some aspects, the non-nicotine vaporizable material (e.g., citric acid) may activate non-nicotine receptors that mimic some of the sensory characteristics of nicotine smoking. For example, the inhalation of the citric acid vapor may provide a throat sensation that is similar to inhaling nicotine vapor and may provide a similar degree of satisfaction for the user. The blinding to whether an individual puff contains nicotine or citric acid may help to maximize the impact of the non-nicotine puffs. Furthermore, the machine learning algorithm may modulate the ratio of nicotinic sensory activation to non-nicotine sensory activation to optimize a sufficient aggregate level of sensory activation to satisfy the user.

While described in many of the aforementioned and following implementations as citric acid, it should be recognized that any non-nicotine chemical or substance that can provide a sensory stimulus which mimics stimuli associated with smoking is suitable. For instance, any non-nicotine vaporizable material that can provide a throat hit sensation can be used. Examples of non-nicotine vaporizable materials in addition to citric acid include ascorbic acid, capsaicin, piperine, and botanical extracts including Aframomum meleguate extract, allspice extract, cedar absolute extract, extract from *Eucalyptus*, eugenol oil, galangal, mustard seed extract, and rosemary extract. A key aspect is that over time the non-nicotine chemical is substituted for the nicotine chemical in steps or increments that the user finds acceptable or can comply with.

The machine learning algorithm may intermittently provide patterns which differ from an expected optimal pattern, and use feedback from the provided patterns to learn whether the patterns should be tuned over time. For instance, the machine learning algorithm may test different patterns to identify a most efficient set of patterns of nicotine/non-nicotine puffs which may maintain compliance with the first and/or second program and yet lead to step down of nicotine consumption and dependency over time.

In some aspects, the machine learning algorithm may identify a level of craving which is consistent with compliance of the first program and/or the second program. The machine learning algorithm may then tune a ratio of nicotine to non-nicotine puffs to stay within a certain level of craving. For instance, for a 10 puff vaporizer session, it may be the case that providing 8 nicotine puffs provides 90% of the satisfaction that 10 nicotine puffs do, providing 5 nicotine puffs provides 80% of the satisfaction that 10 nicotine puffs do, and 3 nicotine puffs provides 20% of the satisfaction. The machine learning algorithm may determine that providing 5 nicotine puffs is optimal for a certain user, because it may cause the user to migrate towards a state of cessation while maintaining a threshold level of satisfaction/craving associated with the first and/or second program. The machine learning algorithm may optionally base this determination not only on the user's behavioral feedback but also at least in part on a pooled feedback from one or more other users on a similar cessation program. For example, based on this feedback, the machine learning algorithm may determine that providing 8 nicotine puffs does not induce migration to lower levels of nicotine consumption, and that providing 3 nicotine puffs does not provide enough satisfaction for the user to maintain compliance with the first program and/or the second program.

Figure 8:
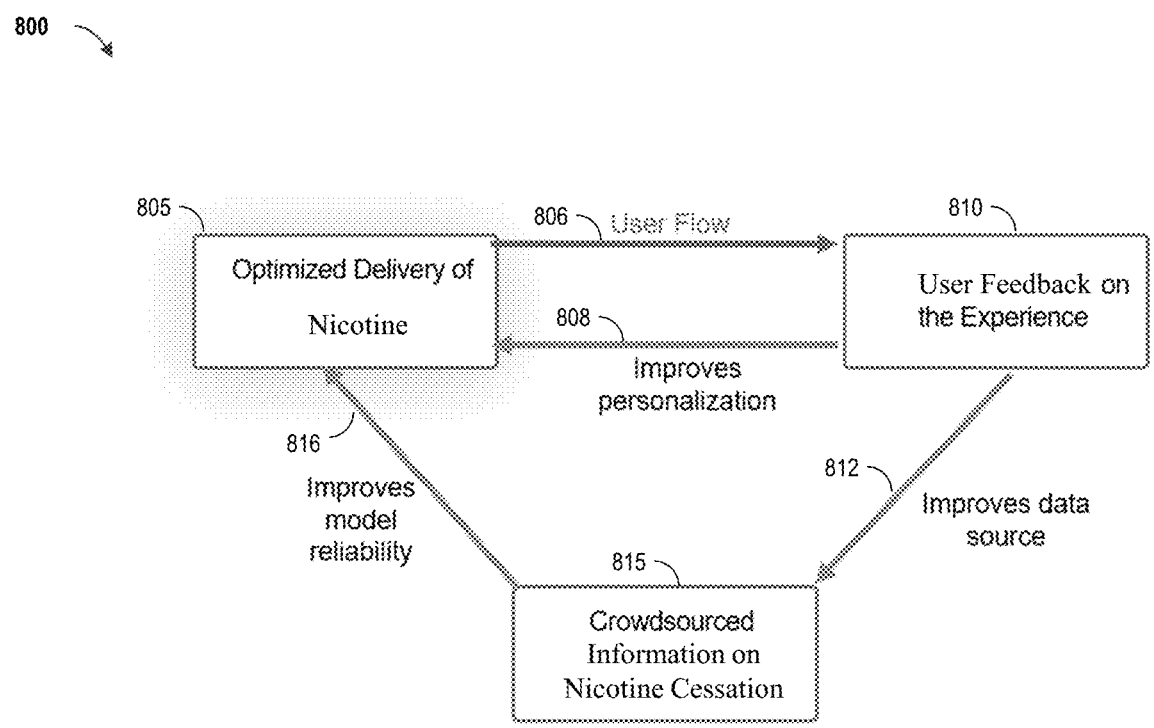
FIG. 8 illustrates a diagram of communications in a network, in accordance with some example implementations.

FIG. 8 is a diagram of communication in a system 800, in accordance with some example implementations. In some implementations, the system 800 (or at least a portion thereof) may include one or more of the vaporizer 100, the vaporizer 200, the user access device 305, an app running on the user access device 305, the remote server 307, the computing apparatus 600, other related apparatuses, and/or some portion thereof.

At 805, the app, vaporizer 100, 200, and/or the computing apparatus 600, for example, may provide an optimized delivery of nicotine to a user. The optimized delivery may include the determined first cartridge and/or first program described herein. For example, the processor 610 may determine the first cartridge and/or first program based on a user selected input received via the user interface 650. In response to providing the optimized delivery of nicotine, the user behavior may be monitored and/or inputted. The monitored and/or inputted data may be transmitted at 806 to a server for analysis or may be analyzed locally at the user access device 305, vaporizer 100, 200, and/or the computing apparatus 600. At 810, the app, vaporizer 100, 200, and/or the computing apparatus 600, for example, may receive user feedback (e.g., monitored and/or inputted data 806) regarding the optimized delivery of nicotine at 805. In some aspects, the processor 610, the display 630, the network interface 640, the user interface 650, the sensor module 660, the I/O filter 670, and/or the antenna 690, may receive and/or process the user feedback. The user feedback may be used to modify the optimized delivery of nicotine to improve user personalization of nicotine delivery. Any modification may be transmitted and/or received by the app, vaporizer 100, 200, and/or the computing apparatus 600 at 808. Additionally, any user feedback and/or modifications to the optimized delivery of nicotine at 805 may be transmitted or retrieved at 812.

At 815, the app, vaporizer 100, 200, and/or the computing apparatus 600, for example, may pool or aggregate the user feedback and/or modifications with crowdsourced information regarding nicotine cessation. In some aspects, the user feedback and/or modifications 812 may improve the pooled data source by providing additional data points associated with previous optimized deliveries. The app, vaporizer 100, 200, and/or the computing apparatus 600, for example, may analyze the user feedback and/or the crowdsourced information to determine that the optimized delivery of nicotine at 805 should be modified. At 816, the app, vaporizer 100, 200, and/or the computing apparatus 600 may modify the optimized delivery of nicotine at 805 and may improve model reliability by adjusting for these additional inputs. For example, the processor 610 may determine that the first cartridge and/or first program should be modified based on the analysis. The processor 610 may then generate or recommend the second cartridge and/or the second program as described herein. The app, vaporizer 100, 200, and/or the computing apparatus 600 may deliver an updated optimized delivery of nicotine at 805.

In some implementations, the app, vaporizer 100, 200, and/or the computing apparatus 600, for example, may also provide additional motivation by providing messaging such as reporting how much of X compound (e.g., nicotine) is consumed, and may show how much money the former smoker is saving by reducing or eliminating smoking. This feedback may be relevant for nicotine, although it may be used for other substances as well. In some implementations, the user may enter their usual price per pack of cigarettes, which may be used as the baseline. This feedback may also be relevant for THC and/or other active substances, since vaping may be a more effective means of consumption of such substances than smoking a material containing the active substance. From anecdotal data, there may be a 5-10× multiplier between smoking and vaping; for example, someone who would vape×mg of THC would otherwise smoke *cannabis* containing 10× mg of THC in a given time interval. Based on dosage monitoring by the device, the vaporizer and/or app may report on savings relative to how much the user otherwise smokes or would otherwise smoke.

In some implementations of the current subject matter, the app may also allow a user to log other health related activities, such as from a fitness app, and/or may suggest correlations between nicotine or THC usage and alcohol consumption, heart rate, blood pressure, workout time or weight changes, etc. For example, a user may enter a preferred unit dose (e.g., using presets, or estimated/recorded/programmable data as described above), and a dosage interval or total daily target. The vaporizer and/or app may then lock out after each dosage, and an alert may pop up on a user computing device (e.g., phone, smartwatch, tablet, etc.) when it's time for a next dosage, with the vaporizer automatically unlocking to allow delivery of this next dosage. Such an approach may be applied as a user-elected reduction approach (step-down or cessation), or to maintain a prescribed therapeutic regimen (e.g., X mg of agent every Y hours, not to exceed Z mg/day).

In some implementations, the vaporizer and/or an affiliated app may have a dashboard style user-interface (e.g., user interface 650), in which users can log on and tabulate their progress over time. Data may be based on individual and/or group data. For example, the group data can show as a population of what the mean smoking-vaping switch rate is at any given time since starting to use a vaporizer. The apparatus may provide a view in which the user can select other users to define a group (cohort) based on their starting conditions: e.g., packs per day, age, gender, etc.

User Preferences.

In some implementations, the vaporizer and/or an affiliated app may be customized based on user preferences, and may provide reminders (including for recreational users, including THC users). For example, in some implementations, the apparatus may save preferences for cartridges (e.g., "pods") of different strains and strength that may be preferred by the user. The app and/or vaporizer may save preferences for different use cases (e.g., 'going for a hike', 'bedtime', 'party time', etc.). In some implementations, in which cartridges come with different THC/CBD ratios, the apparatus (e.g., vaporizer and/or app) may set a reminder of using high or low THC cartridges based on user usage pattern and preferences.

In conjunction with cartridge sensing (as described above), in any of the implementations described herein, the vaporizer and/or app may also or alternatively suggest one or more use profiles (e.g., heating profiles, cessation programs, etc.). For example, based on the type of cartridge and/or based on user input on the type of vaporizable material (strain, concentration, etc.) even in implementations not including cartridge detection, the vaporizer and/or app may suggest a use profile (e.g., "Other users enjoy this strain with profile X", or "Other users enjoy this strain at an initial temperature of 155° C.").

Vaporizer Sessioning.

A vaporizer and/or vaporizer system may include "session" control and/or session metering. In some aspects, a user may find it desirable to monitor and/or control consumption of the vaporizable material, not only for unit dosage described herein, but also for consumption over a certain time period, one or more sessions, and/or the like. Such monitoring and/or control can beneficially allow a user to adjust an amount of vaporizable material available over a certain time period or session, a total time allowed for using the vaporizer, a time period between vaporizer sessions, other consumption settings to meet the needs of the user, and/or the like. In general, vaporizer "session" control and/or session metering is described in U.S. patent application No. 62/590,142, filed on Nov. 22, 2017, and herein incorporated by reference in its entirety.

Software Application Functionality.

As stated above, the vaporizer and/or a device that is part of a vaporizer system can include a user interface (e.g., including an app or application software) that may be executed on a device in communication, which may be configured to determine, display, enforce and/or meter session dosage or sessioning. For example, a vaporizer may have a "session dose" mode/indicator that is displayed on the vaporizer and/or an application. The session dose could be changed by the connected application and/or by directly controlling the vaporizer. For example, a user may want to set a daily nicotine dosage (e.g., 20 mg per day) and gradually decrease that daily dosage over time (e.g., to 10 mg per day). A user may partition the daily dosage into a number of vaporizer sessions allowed per day. For example, the user may set the number of allowed sessions per day to four sessions and set the session dosage to 5 mg of nicotine. The user may then keep the number of vaporizer sessions at four but gradually decrease the session dosage of nicotine to 2.5 mg to help reduce overall nicotine consumption.

In other aspects, the user may want to adjust other configurations of a vaporizer session. For example, in addition to setting a minimum wait time between sessions, the user may also configure blackout periods where the user is unable to start a session (e.g., during the morning or before a regular meeting). Additionally, the user may also set overall nicotine thresholds for a certain time period (e.g., hour, day, week, month, year, etc.) where the vaporizer will not function if the user satisfies the threshold. Additionally, the user may also set certain override procedures to override previously defined rules/thresholds. For example, the user may want to share their device or simply consume more vaporizer material than allowed based on previous settings. The user may enter in a passcode, answer a series of questions, provide other authentication, or otherwise confirm that they wish to override the previous settings.

It also may be desirable for the user interface to provide a visualization of a status of a vaporizer session, daily dosage, or other vapor setting. For example, the user interface may provide a visualization of a virtual pack of cigarettes comprising 20 cigarettes. The virtual pack of cigarettes may correspond to a vaporizer session dosage, daily dosage, or other defined dosage. As the user progresses through a session, the number of cigarettes in the virtual pack of cigarettes may disappear, change color, or otherwise indicate a completion of a portion ($\frac{1}{20}^{th}$) of the session or other dosage. While the above example uses a pack of 20 cigarettes, other numbers of cigarettes and other indications are possible. For example, the number of cigarettes can correspond to the number of vaporizer sessions remaining for the day, week, month, year, etc. Additionally, the visualization may be matches, cigars, lighters, or any other visualization.

Device Control and Customization.

As mentioned above, the vaporizer may be controlled in part by user input to an affiliated app. For example, particular aspects of the vaporizer that may be controlled may include changing a temperature set-point, for example to allows users to get less vapor if they need to be less conspicuous. This may also allow the user to reduce harshness and active ingredient consumption per puff.

The app may also provide a more precise indication of battery level beyond what is displayed on the vaporizer. For example, during charging, the app may indicate time remaining.

As mentioned above, the app may also provide firmware updates to the vaporizer.

For a device that accepts both nicotine and THC cartridges, the affiliated (connected) app may also allow the user to switch between nicotine and THC modes, which may likely have different temperature set points.

A vaporizer and/or a device that is part of a vaporizer system may use received signal strength indicator (rssi) to help a user locate a lost vaporizer. In addition, the app may allow the user to cause the vaporizer to vibrate, flash and/or emit sound(s) as an alarm, including for helping to locate a misplaced apparatus. For example, a temperature change, vibration or flash lights may also be the indicator of whether the vaporizer is hiding nearby. In some implementations, the vaporizer may also help locate a misplaced phone when connected via changing LED colors depending on the distance between the vaporizer and the phone.

A vaporizer and/or an app may be used to adjust LED brightness and color of the vaporizer. For example, for vaporizers with multiple LEDs, a user may download personalized indicator patterns to the device. In addition to making the vaporizer feel more personalized, this may have enhanced utility as it may make it easy to identify which vaporizer belongs to a particular owner.

In some implementations, the temperature of the vaporizer may be adjusted by using a graphical user interface that allows both gross and precise control of the vaporizer temperature with a single finger. For example, a graphical user interface (GUI) may include a display of the temperature visually indicating the current temperature and/or target temperature of the vaporizer; this temperature may be adjusted up or down (within a range). In this example, to adjust the temperature, the user may hold a fingertip in a location on or against the indicator, causing indicators to appear on either side of the temperature when the vaporizing temperature may be adjusted up (on right side) or down (on left side). Quickly sliding a finger over the adjacent indicators may rapidly move the temperature setting in large intervals (e.g., by 3 degree, 5 degree, 10 degree, 15 degree, 20 degrees, 25 degrees, 30 degrees, 35 degrees, etc., intervals). Large interval adjustment is indicated by the large circles. Holding a fingertip on the temperature indicator or adjacent indicators for a predetermined longer period of time (e.g., 1 second, 2 seconds, 3 seconds, 4 second, 5 seconds, etc.) may open a fine temperature control; moving the figure along the fine temperature control may allow increasing/decreasing the selected temperature by fine amounts (e.g., 0.1 degrees, 0.5 degrees, 1 degree, 2 degrees, etc.). The temperature change is shown in the central temperature indicator.

Self-Cleaning.

A vaporizer may be configured to include a self-cleaning mode, in which the vaporizer is configured to operate the heater at a predetermined high temperature (e.g., >=600° F.) for a self-cleaning time (e.g., greater than 1 min, greater than 2 min, greater than 3 min, greater than 4 min, greater than 5 min, greater than 6 min, greater than 7 min, greater than 8 min, greater than 9 min, greater than 10 min, greater than 12 min, greater than 15 min, etc.; or between 1 min and 20 min, between 1 min and 15 min, between 1 min and 10 min, etc.). The self-cleaning mode may be operated directly by the vaporizer, or it may be operated in conjunction with an application (app) or the like.

A self-cleaning mode may be operated in conjunction with an accelerometer or other sensor(s) of a vaporizer. For example, the accelerometer may be used to determine if the vaporizer is not held or carried by the user before entering the self-cleaning operation. For example, self-cleaning may be permitted only when the device has been "still" (e.g., set or held on a resting surface) for a predetermined time period, such as 30 seconds, 1 min, 1.5 min, 2 min, 2.5 min, 3 min, etc. The self-cleaning mode may also only be permitted in implementations (such as shown in FIGS. 2A-2C) having an oven or heating chamber door when the door is secured over the device.

The self-cleaning mode may also be terminated, and the device allowed to cool if the device is picked up or moved (e.g., based on accelerometer input). During self-cleaning, the device may provide a visual, audible or tactile output indicating that self-cleaning is underway. For example, one or more indicators may illuminate or flash (e.g., Red, red and blue, white, etc.) to indicate self-cleaning is operating. In some implementations, the vaporizer may also or alternatively indicate self-heating by emitting a tone, beep, or whine, or the like.

Anti-Theft, Parental Lock, and Child-Resistant Features.

Any of the devices described herein may include a device lock, as mentioned herein. In general, device locking and age/identification verification is described in U.S. patent application No. 62/609,289, filed on Dec. 21, 2017, and herein incorporated by reference in its entirety.

For example, the app (e.g., running on the user device 305) and/or the vaporizer 100, 200 may authenticate to a mobile device (e.g., user device 305) using encryption, as an anti-counterfeit mechanism. A similar scheme may be used to tie the vaporizer 100, 200 to the owner's mobile communications device (e.g., phone, smartwatch, pad, user device 305 etc.), such that if stolen the device is disabled to prevent others from using it. In some implementations, the vaporizer 100, 200 may connect periodically using the network interface 640 to the user device 305 to verify and/or authorize use and/or age of the user. In some implementations, a user may connect to the application on the user device 305 or computer and provide authentication to enable operation of the vaporizer 100, 200. In some aspects, the authentication includes password or PIN entry, a defined gesture (e.g., tap three times), selection of a confirmation button, a voice authentication, or a biometric authentication (e.g., facial recognition) inputted into the application using the user interface 650.

GPS for Locator, Ordering, and Social Networking.

Any of the apparatuses described herein (e.g., vaporizers and/or an affiliated app) may include location services (GPS).

For example, a user buying cartridges for the vaporizer directly from a source may use an app to understand exactly how many cartridges that the user has and how many they have left. A retailer may use this information to offer the user to auto-order more when they are running low.

In any of the apparatuses described herein, the app and/or the vaporizer may include a GPS or may communicate with a GPS to determine location of the vaporizer. Locational information may be used to tell a user the closest retailer to buy more cartridges, to use location service for delivery, to order through smart phone (e.g., usage tracker combined with auto-refill), and/or to inform the user of relevant local legislation about e-cig and *cannabis* use.

In addition, any of the vaporizers and apps described herein may be used to enhance the social experience of the user, including for interaction with other users, and communication with a particular user.

In some implementations, the vaporizer and/or app may profile users and tell them how they compare to others. For example, the vaporizer and/or app may indicate what percentile a user's nicotine/THC consumption fall into and/or may recommend strains (cartridges) based on user behavior (e.g., 'We noticed that you are mostly using your vaporizer at night. Other people who use at night prefer this strain.').

The vaporizer or app may also include access to forums or chat areas where users may trade tips, and areas where physicians can discuss various topics.

In general, any of these apparatuses may permit users to engage in games either by gamification of usage or by including games that may be played by users (including multiple users) unrelated to vaporization of material. For example, gamification of usage (including purchasing of new components such as cartridges) may include awarding points, prizes, etc. and the creation of teams for switching or the like. Games may include the use of the accelerometer or other sensors in the apparatus that may be transmitted wirelessly to an app and/or to another user's vaporizer or app (e.g., directly or via a remote server) to permit game interaction.

The vaporizers and/or apps described herein may also facilitate sponsorships, for example, allowing a user to sign a friend or family member up, pay the cost for a vaporizer, and have it sent to them or even delivered immediately (e.g., by bike messenger). This may be used to provide incentives with sponsors for switching from traditional cigarettes to vaporizers and/or reward use (presumably in place of use of traditional cigarettes), e.g., if you stick with it you get prizes (e.g., gift cards, etc.).

Any of the apparatuses described herein (including the vaporizers and any affiliated apps) may also be used to collect and analyze user data. This may allow the vaporizer producers, providers and retailers to get to know users better, including understand where when and how they are using the vaporizer. Knowing where and when a consumer is using a vaporizer may allow better marketing to users and may improve the design for future products.

The vaporizers and apps described herein may also facilitate communication between the manufacturer and/or retailer and the consumer (user). For example, by interacting with consumers while they are using the product, there may be opportunities to encourage direct sales. Thus, for example an app may say: "If my calculations are correct, it looks like you only have one cartridge left in your pack. Would you like to buy another?"

The vaporizers and apps described herein may also have enhanced anti-counterfeit components, including registration (e.g., through use of the app) of the vaporizer and/or app. In some implementations, the vaporizer could have a similar encryption handshake with the app and/or the charging dock.

In addition, the vaporizers and/or the app may permit or include device diagnostics. For example, the vaporizer and/or app may monitor component level failures (e.g., pressure sensor, battery, pogo pins, etc.), and may potentially identify a broken device in the field and ship warranty replacement without the need to return device to customer service. This may also permit the faster collection of data on common problems to be used for rolling changes and future designs.

Example: Application Software/Hardware/Firmware ("App")

Examples of application software with many of the features described herein for use with one or more vaporizers are described with reference to FIG. 9. Each of the user interface (UI) screens described herein in FIG. 9 can be generated by user interface 650 of a user device 305, and/or the computing apparatus 600. For example, the user device 305 can comprise the memory 620 storing instructions for executing the vaporizer application running on the user device 305. The processor 610 can execute those instructions and can generate the exemplary UIs using the display 630 and/or the user interface 650. The exemplary UIs can also be generated based on user input received via the display 630 and/or the user interface 650. The exemplary UIs can also be generated based on communications with the vaporizer 100, 200, remote server 307, other user devices 305, and/or other devices. The communications can be received using the network interface 640 and/or antenna 690 of the user device 305, the vaporizer 100, 200, and/or any other device.

Figure 9:
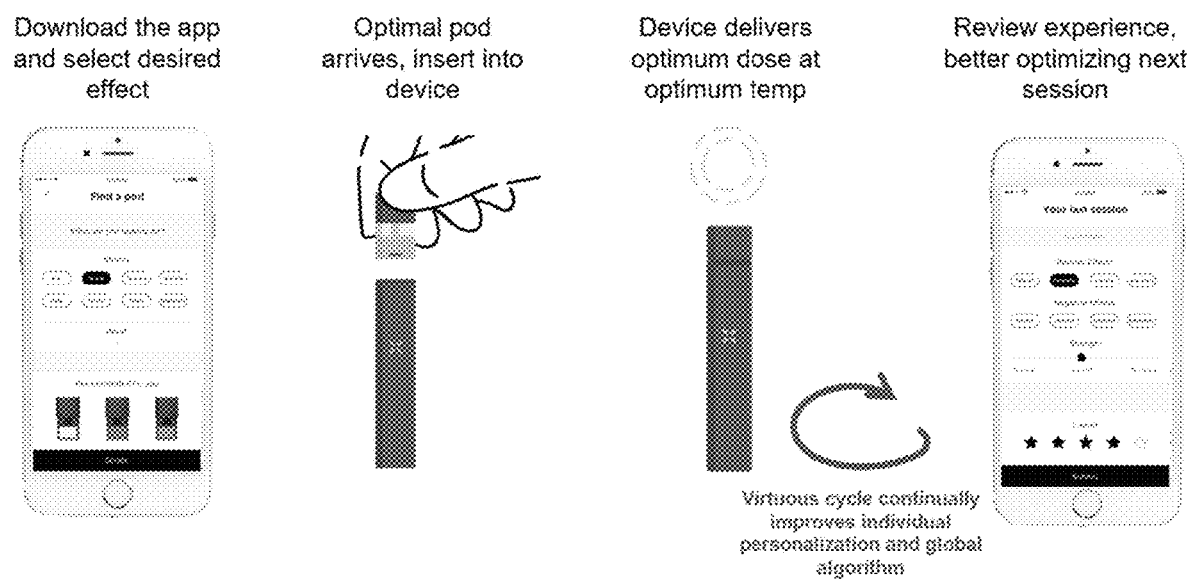
FIG. 9 illustrates a flowchart depicting features of implementing user experiences, in accordance with some example implementations.

FIG. 9 shows a user interface (UI) for an application (app) that may be used with a vaporizer as described herein, including an initial download of the app and a selection of a desired effect, such as quitting smoking combustible cigarettes, an insertion of an optimized pod for achieving the selected desired effect, delivery of an optimum dose/temperature, and feedback regarding user experience with the device, pod, dose, and/or the like.

Any of the apps described herein may also be adapted for use with detection, including automatic detection, of the cartridge and/or vaporizable material. The app may provide instructions for detecting/identifying, or the operation of the app may be automatically adjusted/customized based on the detected cartridge, beacon, second device, and/or the like.

Aerosolizable Material.

As described above, a vaporizer and/or vaporizer system consistent with implementations of the current subject matter may be used with (and may include or be configured specifically for) any appropriate vaporizable material. In general, vaporizable material is described in U.S. patent application Ser. No. 15/605,890, filed on May 25, 2017, and herein incorporated by reference in its entirety.

For example, in certain implementations, the vaporizable material is an organic material. In certain examples, vaporizable material includes a liquid, a viscous liquid, a wax, a loose-leaf plant material, etc. In certain examples, the vaporizable material is a tobacco-based material. In certain examples, the vaporizable material is a *Cannabis*-based material. In certain examples, the vaporizable material is a botanical. In certain examples, the vaporizable material is nicotine, a nicotine derivative or a nicotine salt. In certain examples, the vaporizable material is a nutraceutical. In certain examples, the vaporizable material contains a cannabinoid. In certain examples, the vaporizable material is a medicinal compound. In certain examples, the vaporizable material is a non-nicotine material. In certain examples, the vaporizable material is a citric acid compound.

Figure 10:
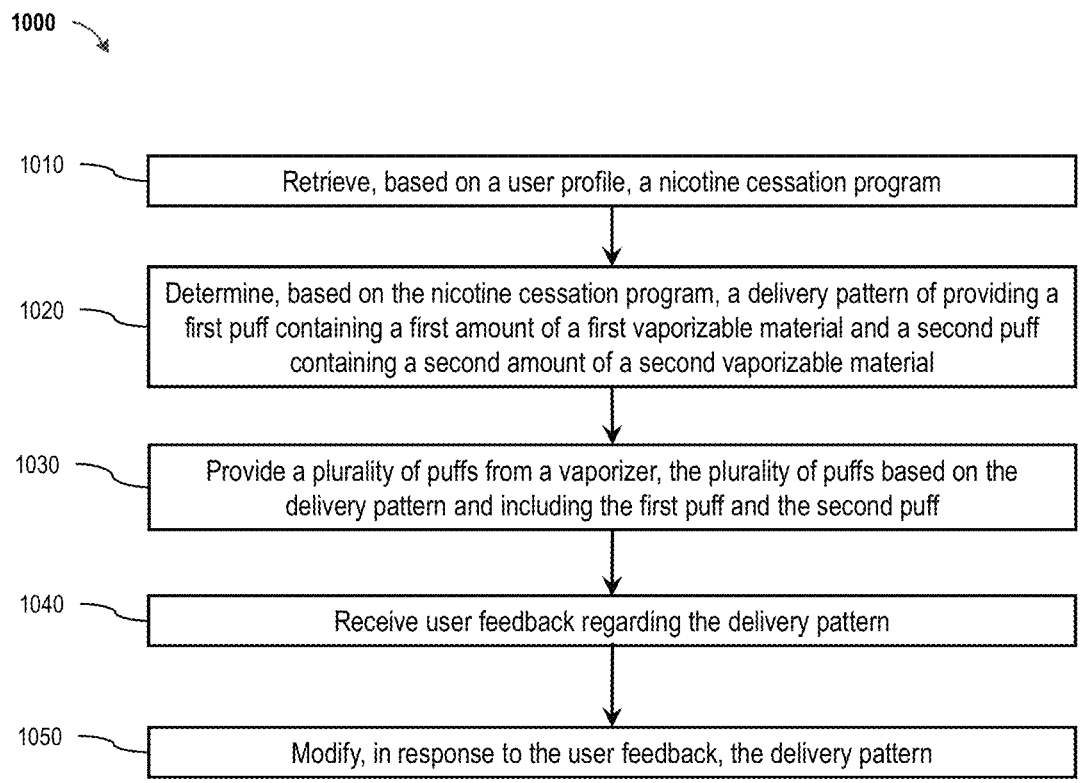
FIG. 10 illustrates a flowchart of a method for nicotine cessation, in accordance with some example implementations.

As noted above, implementations of the current subject matter include various methods of use of vaporizers and vaporizer systems that include a device in communication with a vaporizer. FIG. 10 illustrates a flowchart of a method 1000 for nicotine cessation. In various implementations, the method 1000 (or at least a portion thereof) may be performed by one or more of the vaporizer 100, the vaporizer 200, the user access device 305, an app running on the user access device 305, the remote server 307, the computing apparatus 600, other related apparatuses, and/or some portion thereof.

Method 1000 may start at operational block 1010 where the apparatus 600, for example, may retrieve, based on a user profile, a nicotine cessation program. In some aspects, the retrieving may be in response to receiving a selection to initiate a vaporizer session. In some aspects, the user profile may be created when the user first downloads an app associated with the vaporizer. The nicotine cessation program may be generated when the user selects a desired effect (e.g., nicotine cessation) when using the vaporizer. In some implementations, the user profile may include the nicotine cessation program. Method 1000 may proceed to operational block 1020 where the apparatus 600, for example, may determine, based on the nicotine cessation program, a delivery pattern of providing a first puff containing a first amount of a first vaporizable material (e.g., nicotine) and a second puff containing a second amount of a second vaporizable material (e.g., citric acid). In some aspects, the delivery pattern may include toggling between a first reservoir 120 holding the first vaporizable material and a second reservoir 120 holding the second vaporizable material. Such toggling may allow the apparatus 600 to switch between providing nicotine and non-nicotine puffs based on the delivery pattern and/or cessation program.

Method 1000 may proceed to operational block 1030 where the apparatus 600, for example, may provide a plurality of puffs from a vaporizer. The plurality of puffs may be based on the delivery pattern and may include the first puff and the second puff. In some aspects, the providing may include providing the determined delivery pattern in a blind manner such that the user of the vaporizer is unaware of which vaporizable material is being provided in a given puff. Method 1000 may proceed to operational block 1040 where the apparatus 600, for example, may receive user feedback regarding the determined delivery pattern provided. The user feedback may include a gesture using the vaporizer, an input on a user interface, a monitored behavior of the vaporizer and/or user, and/or the like. In some aspects, the method 1000 may optionally include updating the user profile and/or the nicotine cessation program based on the user feedback. The method 1000 may proceed to operational block 1040 where the apparatus 600, for example, may modify the delivery pattern based on the user feedback. The updating may include adjusting a quantity, an order, a size, a consistency, and/or the like of the first puff and/or the second puff in the delivery pattern. In some aspects, the updating may be further based at least in part on pooled feedback from a plurality of other users.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to a given example, the features and elements so described or shown can apply to other implementations of the current subject matter. It will also be appreciated by those of skill in the art that references to a structure or feature that is disposed "adjacent" another feature may have portions that overlap or underlie the adjacent feature.

Terminology used herein is for the purpose of describing particular implementations and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification and in the claims, specify the presence of stated features, steps, operations, elements, and/or components, but do not preclude the presence or addition of one or more other features, steps, operations, elements, components, and/or groups thereof.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative implementations are described above, any of a number of changes may be made to various implementations without departing from the teachings herein. For example, the order in which various described method steps are performed may often be changed in alternative implementations, and in other alternative implementations one or more method steps may be skipped altogether. Optional features of various device and system implementations may be included in some implementations and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like The examples and illustrations included herein show, by way of illustration and not of limitation, specific implementations in which the subject matter may be practiced. As mentioned, other implementations may be utilized and derived there from, such that structural and logical substitutions and changes may be made without departing from the scope of this disclosure. Such implementations of the inventive subject matter may be referred to herein individually or collectively by the term "invention" merely for convenience and without intending to voluntarily limit the scope of this application to any single invention or inventive concept, if more than one is, in fact, disclosed. Thus, although specific implementations have been illustrated and described herein, any arrangement calculated to achieve the same purpose may be substituted for the specific implementations shown. This disclosure is intended to cover any and all adaptations or variations of various implementations. Combinations of the above implementations, and other implementations not specifically described herein, will be apparent to those of skill in the art upon reviewing the above description.

I claim:

1. A method comprising:
 determining, by one or more processors, a delivery pattern in which a first quantity of puffs of a first aerosolizable material comprising nicotine alternate with a second quantity of puffs of a second aerosolizable material comprising citric acid, wherein the second aerosolizable material does not include nicotine, wherein determining the delivery pattern includes determining a ratio between the first quantity of puffs and the second quantity of puffs to deliver a quantity of nicotine over a time period;

providing, based on the delivery pattern, the first quantity of puffs alternating with the second quantity of puffs;

receiving, by the one or more processors and in response to the providing, user feedback associated with the delivery pattern; and modifying, by the one or more processors and based on the user feedback, the delivery pattern, wherein modifying the delivery patterns comprises intermittently providing modified delivery patterns which differ from an expected optimal delivery pattern, and modifying, based on user feedback from the provided patterns, the delivery pattern, wherein individual modified delivery pattern comprises a sequence of providing the first aerosolizable material alternating with the second aerosolizable material, wherein the individual modified delivery pattern is different from the expected optimal delivery pattern, the expected optimal delivery pattern comprising a sequence of providing the first aerosolizable material alternating with the second aerosolizable material.

2. The method of claim 1, wherein modifying the delivery pattern comprises decreasing the first quantity of puffs in the ratio to reduce the quantity of nicotine delivered over the time period.

3. The method of claim 1, wherein the first quantity of puffs in the delivery pattern is different from the second quantity of puffs in the delivery pattern.

4. The method of claim 1, wherein modifying the delivery pattern comprises adjusting a consistency of the first quantity of puffs and/or the second quantity of puffs in the delivery pattern.

5. The method of claim 1, wherein determining the delivery pattern is based on a user profile, the user profile comprising a program for reducing consumption of combustible cigarettes and/or nicotine.

6. The method of claim 1, wherein providing the first quantity of puffs alternating with the second quantity of puffs comprises:

heating the first aerosolizable material in a first reservoir of a cartridge to generate each puff of the first quantity of puffs; and heating the second aerosolizable material in a second reservoir of the cartridge to generate each puff of the second quantity of puffs.

7. The method of claim 1, wherein determining the delivery pattern is based on receiving the user feedback via user interaction with a user interface.

8. The method of claim 7, wherein receiving the user feedback comprises processing the user interaction by an application executing on the one or more processors.

9. The method of claim 7, wherein the user input comprises at least one of: an age, a height, a weight, an ethnicity, a location, a type of current smoking devices used, a current smoking/tobacco/nicotine use, a past smoking/tobacco/nicotine use, a current and/or a past vaporizer use, a user behavior, a length of smoking/tobacco/nicotine use, an eating habit, an exercise habit, a motivation for quitting smoking, a personality type, a time period, a desired reduction in nicotine, and a flavor preference.

10. The method of claim 1, wherein the user feedback comprises at least one of: a current level of satisfaction, a craving, or a desire for a cigarette, a time since last combusted cigarette, a number of cigarettes smoked per day, a level of satisfaction after an aerosolizer puff, a location of cigarette use, an activity that accompanied the cigarette use, whether the user smoked the cigarette alone or in a group, and a time of day of cigarette use.

11. The method of claim 1, wherein receiving the user feedback comprises receiving the user feedback from at least one of: an application executing on the one or more processors, a sensor detecting a gesture of the aerosolizer, a sensor detecting a gesture of a user, a touch sensor, a motion sensor, a selection of an input on the aerosolizer and/or a user interface, and a processor determining learned behavior from past user interaction with the aerosolizer.

12. The method of claim 1, wherein modifying the delivery pattern comprises adjusting a quantity of the first quantity of puffs and/or a quantity of the second quantity of puffs in the delivery pattern.

13. The method of claim 1, wherein modifying the delivery pattern comprises tuning the delivery pattern based on a machine learning algorithm.

14. The method of claim 1, wherein modifying the delivery pattern comprises updating the delivery pattern based on the user feedback and feedback received from a plurality of other users.

15. The method of claim 1, wherein determining the delivery pattern further includes determining a concentration of nicotine in each puff of the first quantity of puffs such that the quantity of nicotine is delivered over the time period.

16. The method of claim 1, wherein modifying the delivery pattern comprises applying a machine learning model to tune, based on the user feedback, the ratio to a level sufficient to satisfy a user craving for nicotine.

17. A vaporizer comprising:

at least one processor; and at least one memory storing instructions which, when executed by the at least one processor, cause the vaporizer to at least:

determine, by one or more processors, a delivery pattern in which a first quantity of puffs of a first aerosolizable material comprising nicotine alternate with a second quantity of puffs of a second aerosolizable material comprising citric acid, wherein the second aerosolizable material does not include nicotine, wherein the delivery pattern includes a ratio between the first quantity of puffs and the second quantity of puffs to deliver a quantity of nicotine is delivered over a time period;

provide, based on the delivery pattern, the first quantity of puffs alternating with the second quantity of puffs;

receive, by the one or more processors and in response to the providing, user feedback associated with the delivery pattern; and modify, by the one or more processors and based on the user feedback, the delivery pattern, wherein modifying the delivery patterns comprises intermittently providing modified delivery patterns which differ from an expected optimal delivery pattern, and modifying, based on user feedback from the provided patterns, the delivery pattern, wherein individual modified delivery pattern comprises a sequence of providing the first aerosolizable material alternating with the second aerosolizable material, wherein the individual modified delivery pattern is different from the expected optimal delivery pattern, the expected optimal delivery pattern comprising a sequence of providing the first aerosolizable material alternating with the second aerosolizable material.

18. The vaporizer of claim 17, wherein the delivery pattern is modified based on decreasing the first quantity of puffs in the ratio to reduce the quantity of nicotine delivered over the time period.

19. The vaporizer of claim 17, wherein the first quantity of puffs in the delivery pattern is different from the second quantity of puffs in the delivery pattern.

20. The vaporizer of claim 17, wherein the delivery pattern is determined based on a user profile, the user profile comprising a program for reducing consumption of combustible cigarettes and/or nicotine.

21. The vaporizer of claim 17, wherein the first quantity of puffs alternating with the second quantity of puffs are provided based on the vaporizer being further caused to at least:
 heat the first aerosolizable material in a first reservoir of a cartridge to generate each puff of the first quantity of puffs; and
 heat the second aerosolizable material in a second reservoir of the cartridge to generate each puff of the second quantity of puffs.

22. The vaporizer of claim 17, wherein the delivery pattern is determined based on receiving the user feedback by interaction of the user with a user interface.

23. The vaporizer of claim 17, wherein the delivery pattern further includes a concentration of nicotine in each puff of the first quantity of puffs such that the quantity of nicotine is delivered over the time period.

24. The vaporizer of claim 17, wherein the delivery pattern is modified based on applying a machine learning model to tune, based on the user feedback, the ratio to a level sufficient to satisfy a user craving for nicotine.

\* \* \* \* \*